(12) United States Patent
Stein et al.

(10) Patent No.: US 12,213,893 B2
(45) Date of Patent: Feb. 4, 2025

(54) LORDOTIC EXPANDABLE INTERBODY IMPLANT AND METHOD OF USING SAME

(71) Applicant: NuVasive, Inc., San Diego, CA (US)

(72) Inventors: Christopher Stein, Fallbrook, CA (US); Seth Gustine, Encinitas, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 18/321,043

(22) Filed: May 22, 2023

(65) Prior Publication Data

US 2023/0285164 A1 Sep. 14, 2023

Related U.S. Application Data

(63) Continuation of application No. 16/667,766, filed on Oct. 29, 2019, now Pat. No. 11,696,836, which is a continuation of application No. 15/799,554, filed on Oct. 31, 2017, now Pat. No. 10,492,924, which is a continuation of application No. 14/456,640, filed on Aug. 11, 2014, now Pat. No. 9,801,734.

(60) Provisional application No. 61/864,132, filed on Aug. 9, 2013.

(51) Int. Cl.
*A61F 2/44* (2006.01)
*A61F 2/30* (2006.01)

(52) U.S. Cl.
CPC .... *A61F 2/447* (2013.01); *A61F 2002/30158* (2013.01); *A61F 2002/30387* (2013.01); *A61F 2002/30471* (2013.01); *A61F 2002/30507* (2013.01); *A61F 2002/30538* (2013.01); *A61F 2002/30904* (2013.01)

(58) Field of Classification Search
CPC ........................................................ A61F 2/44
See application file for complete search history.

(56) References Cited

U.S. PATENT DOCUMENTS

| | | |
|---|---|---|
| 2,702,031 A | 2/1955 | Wenger |
| 3,111,945 A | 11/1963 | Solbrig |
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |

(Continued)

FOREIGN PATENT DOCUMENTS

| | | |
|---|---|---|
| AU | 765774 | 3/2002 |
| AU | 2004100977 | 12/2004 |

(Continued)

OTHER PUBLICATIONS

Abe et al., "Experimental external fixation combined with percutaneous discectomy in the management of scoliosis.", Spine, 1999, pp. 646-653, 24, No. 7.

(Continued)

*Primary Examiner* — David W Bates

(57) ABSTRACT

An expandable spinal fusion implant including a housing, upper and lower endplates, a wedge positioned within the housing and between the upper and lower endplates and a drive mechanism to urge the wedge distally between the upper and lower endplates to increase the separation between the endplates and expand the overall height of the distal end of the implant.

19 Claims, 18 Drawing Sheets

(56) References Cited

U.S. PATENT DOCUMENTS

| | | |
|---|---|---|
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,759,769 A | 7/1988 | Hedman et al. |
| 4,854,304 A | 8/1989 | Zielke |
| 4,863,476 A | 9/1989 | Shepperd |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,554,191 A | 9/1996 | Lahille et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,653,763 A | 8/1997 | Errico et al. |
| 5,658,335 A | 8/1997 | Allen |
| 5,659,217 A | 8/1997 | Petersen |
| 5,662,683 A | 9/1997 | Kay |
| 5,665,122 A | 9/1997 | Kambin |
| 5,669,909 A | 9/1997 | Zdeblick et al. |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| D390,592 S | 2/1998 | Agata |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,776,199 A | 7/1998 | Michelson |
| 5,782,832 A | 7/1998 | Larsen et al. |
| 5,782,919 A | 7/1998 | Zdeblick et al. |
| D397,439 S | 8/1998 | Koros et al. |
| 5,810,815 A | 9/1998 | Morales |
| 5,827,286 A | 10/1998 | Incavo et al. |
| 5,830,221 A | 11/1998 | Stein et al. |
| 5,865,848 A | 2/1999 | Baker |
| 5,879,375 A | 3/1999 | Larson, Jr. et al. |
| 5,893,889 A | 4/1999 | Harrington |
| 5,902,304 A | 5/1999 | Walker et al. |
| 5,935,127 A | 8/1999 | Border |
| 5,935,129 A | 8/1999 | McDevitt et al. |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 5,980,522 A | 11/1999 | Koros et al. |
| 6,022,349 A | 2/2000 | McLeod et al. |
| 6,033,412 A | 3/2000 | Losken et al. |
| 6,034,296 A | 3/2000 | Elvin et al. |
| 6,045,579 A | 4/2000 | Hochshuler et al. |
| 6,080,193 A | 6/2000 | Hochshuler et al. |
| 6,102,922 A | 8/2000 | Jakobsson et al. |
| 6,102,950 A | 8/2000 | Vaccaro |
| 6,106,525 A | 8/2000 | Sachse |
| 6,117,174 A | 9/2000 | Nolan |
| 6,126,660 A | 10/2000 | Dietz |
| 6,126,661 A | 10/2000 | Faccioli et al. |
| 6,129,763 A | 10/2000 | Chauvin .......... A61F 2/4455 623/17.11 |
| 6,138,681 A | 10/2000 | Chen et al. |
| 6,139,316 A | 10/2000 | Sachdeva et al. |
| 6,162,223 A | 12/2000 | Orsak et al. |
| 6,176,882 B1 | 1/2001 | Biedermann et al. |
| 6,179,873 B1 | 1/2001 | Zientek |
| 6,183,476 B1 | 2/2001 | Gerhardt et al. |
| 6,190,414 B1 | 2/2001 | Young et al. |
| 6,200,317 B1 | 3/2001 | Aalsma et al. |
| 6,214,050 B1 | 4/2001 | Huene |
| 6,217,579 B1 | 4/2001 | Koros |
| 6,234,956 B1 | 5/2001 | He et al. |
| 6,241,730 B1 | 6/2001 | Alby |
| 6,245,075 B1 | 6/2001 | Betz et al. |
| 6,302,914 B1 | 10/2001 | Michelson |
| 6,315,784 B1 | 11/2001 | Djurovic |
| 6,319,255 B1 | 11/2001 | Grundei et al. |
| 6,331,744 B1 | 12/2001 | Chen et al. |
| H2009 H | 1/2002 | Martin et al. |
| 6,336,929 B1 | 1/2002 | Justin |
| 6,340,369 B1 | 1/2002 | Ferree |
| 6,343,568 B1 | 2/2002 | McClasky |
| 6,344,058 B1 | 2/2002 | Ferree |
| 6,350,126 B1 | 2/2002 | Levisman |
| 6,352,557 B1 | 3/2002 | Ferree |
| 6,355,069 B1 | 3/2002 | DeCarlo, Jr. et al. |
| 6,358,283 B1 | 3/2002 | Hogfors et al. |
| 6,368,351 B1 | 4/2002 | Glenn et al. |
| 6,371,989 B1 | 4/2002 | Chauvin et al. |
| 6,375,655 B1 | 4/2002 | Zdeblick et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,419,702 B1 | 7/2002 | Ferree |
| 6,436,140 B1 | 8/2002 | Liu et al. |
| 6,436,142 B1 | 8/2002 | Paes et al. |

(56) References Cited

U.S. PATENT DOCUMENTS

| | | | |
|---|---|---|---|
| 6,443,989 | B1 | 9/2002 | Jackson |
| 6,443,990 | B1 | 9/2002 | Aebi et al. |
| 6,447,544 | B1 | 9/2002 | Michelson |
| 6,447,547 | B1 | 9/2002 | Michelson |
| 6,451,057 | B1 | 9/2002 | Chen et al. |
| 6,454,806 | B1 | 9/2002 | Cohen et al. |
| 6,454,807 | B1 | 9/2002 | Jackson ............... A61F 2/447 623/17.15 |
| 6,471,724 | B2 | 10/2002 | Zdeblick et al. |
| 6,478,823 | B1 | 11/2002 | Michelson |
| 6,491,724 | B1 | 12/2002 | Ferree |
| 6,499,907 | B1 | 12/2002 | Baur |
| 6,500,110 | B1 | 12/2002 | Davey et al. |
| 6,506,051 | B2 | 1/2003 | Levisman |
| 6,508,820 | B2 | 1/2003 | Bales |
| 6,510,345 | B1 | 1/2003 | Van Bentem |
| 6,520,991 | B2 | 2/2003 | Huene |
| 6,533,791 | B1 | 3/2003 | Betz et al. |
| 6,537,196 | B1 | 3/2003 | Creighton, IV et al. |
| 6,554,831 | B1 | 4/2003 | Rivard et al. |
| 6,562,074 | B2 | 5/2003 | Gerbec et al. |
| 6,565,573 | B1 | 5/2003 | Ferrante et al. |
| 6,565,576 | B1 | 5/2003 | Stauch et al. |
| 6,576,016 | B1 | 6/2003 | Hochshuler et al. |
| 6,579,290 | B1 | 6/2003 | Hardcastle et al. |
| 6,582,313 | B2 | 6/2003 | Perrow |
| 6,583,630 | B2 | 6/2003 | Mendes et al. |
| 6,613,091 | B1 | 9/2003 | Zdeblick et al. |
| 6,613,093 | B2 | 9/2003 | DeCarlo, Jr. et al. |
| 6,616,669 | B2 | 9/2003 | Ogilvie et al. |
| 6,626,917 | B1 | 9/2003 | Craig |
| 6,641,614 | B1* | 11/2003 | Wagner ............... A61F 2/4455 623/17.15 |
| 6,645,206 | B1 | 11/2003 | Zdeblick et al. |
| 6,648,917 | B2 | 11/2003 | Gerbec et al. |
| 6,648,918 | B2 | 11/2003 | Ferree |
| 6,656,135 | B2 | 12/2003 | Zogbi et al. |
| 6,656,194 | B1 | 12/2003 | Gannoe et al. |
| 6,666,891 | B2 | 12/2003 | Boehm, Jr. et al. |
| 6,667,725 | B1 | 12/2003 | Simons et al. |
| 6,673,079 | B1 | 1/2004 | Kane |
| 6,685,742 | B1 | 2/2004 | Jackson |
| 6,695,851 | B2 | 2/2004 | Zdeblick et al. |
| 6,702,816 | B2 | 3/2004 | Buhler |
| 6,706,042 | B2 | 3/2004 | Taylor |
| 6,706,070 | B1 | 3/2004 | Wagner et al. |
| 6,709,293 | B2 | 3/2004 | Mori et al. |
| 6,719,796 | B2 | 4/2004 | Cohen et al. |
| 6,719,797 | B1 | 4/2004 | Ferree |
| 6,730,087 | B1 | 5/2004 | Butsch |
| 6,730,126 | B2 | 5/2004 | Boehm, Jr. et al. |
| 6,733,535 | B2 | 5/2004 | Michelson |
| 6,743,255 | B2 | 6/2004 | Ferree |
| 6,761,503 | B2 | 7/2004 | Breese |
| 6,769,499 | B2 | 8/2004 | Cargill et al. |
| 6,773,460 | B2 | 8/2004 | Jackson |
| 6,789,442 | B2 | 9/2004 | Forch |
| 6,796,984 | B2 | 9/2004 | Soubeiran |
| 6,802,844 | B2 | 10/2004 | Ferree |
| 6,809,434 | B1 | 10/2004 | Duncan et al. |
| 6,821,298 | B1 | 11/2004 | Jackson |
| 6,835,206 | B2 | 12/2004 | Jackson |
| 6,835,207 | B2 | 12/2004 | Zacouto et al. |
| 6,852,113 | B2 | 2/2005 | Nathanson et al. |
| 6,852,129 | B2 | 2/2005 | Gerbec et al. |
| 6,863,673 | B2 | 3/2005 | Gerbec et al. |
| 6,905,512 | B2 | 6/2005 | Paes et al. |
| 6,918,838 | B2 | 7/2005 | Schwarzler et al. |
| 6,918,910 | B2 | 7/2005 | Smith et al. |
| 6,921,400 | B2 | 7/2005 | Sohngen |
| 6,923,951 | B2 | 8/2005 | Contag et al. |
| 6,955,691 | B2 | 10/2005 | Chae et al. |
| 6,971,143 | B2 | 12/2005 | Domroese |
| 7,001,346 | B2 | 2/2006 | White |
| 7,008,425 | B2 | 3/2006 | Phillips |
| 7,011,658 | B2 | 3/2006 | Young |
| 7,029,472 | B1 | 4/2006 | Fortin |
| 7,029,475 | B2 | 4/2006 | Panjabi |
| 7,041,105 | B2 | 5/2006 | Michelson |
| 7,060,080 | B2 | 6/2006 | Bachmann |
| 7,063,706 | B2 | 6/2006 | Wittenstein |
| 7,066,961 | B2 | 6/2006 | Michelson |
| 7,070,598 | B2 | 7/2006 | Lim et al. |
| 7,087,055 | B2 | 8/2006 | Lim et al. |
| 7,105,029 | B2 | 9/2006 | Doubler et al. |
| 7,105,968 | B2 | 9/2006 | Nissen |
| 7,114,501 | B2 | 10/2006 | Johnson et al. |
| 7,115,129 | B2 | 10/2006 | Heggeness |
| 7,128,760 | B2 | 10/2006 | Michelson |
| 7,135,022 | B2 | 11/2006 | Kosashvili et al. |
| 7,156,874 | B2 | 1/2007 | Paponneau et al. |
| 7,160,312 | B2 | 1/2007 | Saadat |
| 7,163,538 | B2 | 1/2007 | Altarac et al. |
| 7,189,005 | B2 | 3/2007 | Ward |
| 7,191,007 | B2 | 3/2007 | Desai et al. |
| 7,204,853 | B2 | 4/2007 | Gordon et al. |
| 7,211,112 | B2 | 5/2007 | Baynham et al. |
| 7,217,291 | B2 | 5/2007 | Zucherman et al. |
| 7,217,293 | B2 | 5/2007 | Branch, Jr. |
| 7,218,232 | B2 | 5/2007 | DiSilvestro et al. |
| 7,220,280 | B2 | 5/2007 | Kast et al. |
| 7,238,186 | B2 | 7/2007 | Zdeblick et al. |
| 7,238,191 | B2 | 7/2007 | Bachmann |
| 7,241,300 | B2 | 7/2007 | Sharkawy et al. |
| 7,243,719 | B2 | 7/2007 | Baron et al. |
| 7,255,682 | B1 | 8/2007 | Bartol, Jr. et al. |
| 7,282,023 | B2 | 10/2007 | Frering |
| 7,282,063 | B2 | 10/2007 | Cohen et al. |
| 7,285,087 | B2 | 10/2007 | Moaddeb et al. |
| 7,302,015 | B2 | 11/2007 | Kim et al. |
| 7,302,858 | B2 | 12/2007 | Walsh et al. |
| 7,314,443 | B2 | 1/2008 | Jordan et al. |
| 7,316,714 | B2 | 1/2008 | Gordon et al. |
| 7,333,013 | B2 | 2/2008 | Berger |
| 7,357,037 | B2 | 4/2008 | Hnat et al. |
| 7,357,635 | B2 | 4/2008 | Belfor et al. |
| 7,360,542 | B2 | 4/2008 | Nelson et al. |
| 7,390,007 | B2 | 6/2008 | Helms et al. |
| 7,390,294 | B2 | 6/2008 | Hassler, Jr. |
| 7,402,134 | B2 | 7/2008 | Moaddeb et al. |
| 7,402,176 | B2 | 7/2008 | Malek |
| 7,410,501 | B2 | 8/2008 | Michelson |
| 7,429,259 | B2 | 9/2008 | Cadeddu et al. |
| 7,431,735 | B2 | 10/2008 | Liu et al. |
| 7,445,010 | B2 | 11/2008 | Kugler et al. |
| 7,445,636 | B2 | 11/2008 | Michelson |
| 7,458,981 | B2 | 12/2008 | Fielding et al. |
| 7,485,149 | B1 | 2/2009 | White |
| 7,489,495 | B2 | 2/2009 | Stevenson |
| 7,503,933 | B2 | 3/2009 | Michelson |
| 7,530,981 | B2 | 5/2009 | Kutsenko |
| 7,531,002 | B2 | 5/2009 | Sutton et al. |
| 7,547,308 | B2 | 6/2009 | Bertagnoli et al. |
| 7,553,298 | B2 | 6/2009 | Hunt et al. |
| 7,561,916 | B2 | 7/2009 | Hunt et al. |
| 7,569,074 | B2 | 8/2009 | Eisermann et al. |
| 7,588,599 | B2 | 9/2009 | Sweeney |
| 7,611,526 | B2 | 11/2009 | Carl et al. |
| 7,618,435 | B2 | 11/2009 | Opolski |
| 7,618,458 | B2 | 11/2009 | Biedermann et al. |
| 7,621,951 | B2 | 11/2009 | Glenn et al. |
| 7,621,958 | B2 | 11/2009 | Zdeblick et al. |
| 7,655,043 | B2 | 2/2010 | Peterman et al. |
| 7,655,046 | B2 | 2/2010 | Dryer et al. |
| 7,658,754 | B2 | 2/2010 | Zhang et al. |
| 7,666,184 | B2 | 2/2010 | Stauch |
| 7,666,210 | B2 | 2/2010 | Franck et al. |
| 7,674,265 | B2 | 3/2010 | Smith ............... A61B 17/1671 606/79 |
| 7,678,136 | B2 | 3/2010 | Doubler et al. |
| 7,678,139 | B2 | 3/2010 | Garamszegi et al. |
| 7,678,148 | B2 | 3/2010 | Peterman |
| 7,703,727 | B2 | 4/2010 | Selness |
| 7,704,279 | B2 | 4/2010 | Moskowitz et al. |

(56) References Cited

U.S. PATENT DOCUMENTS

| | | |
|---|---|---|
| 7,708,737 B2 | 5/2010 | Kraft et al. |
| 7,708,762 B2 | 5/2010 | McCarthy et al. |
| 7,708,778 B2 | 5/2010 | Gordon et al. |
| 7,722,674 B1 | 5/2010 | Grotz |
| 7,727,143 B2 | 6/2010 | Birk et al. |
| 7,727,280 B2 | 6/2010 | McLuen |
| 7,731,751 B2 | 6/2010 | Butler et al. |
| 7,749,270 B2 | 7/2010 | Peterman |
| 7,749,279 B2 | 7/2010 | Twomey et al. |
| 7,753,913 B2 | 7/2010 | Szakelyhidi, Jr. et al. |
| 7,753,915 B1 | 7/2010 | Eksler et al. |
| 7,753,958 B2 | 7/2010 | Gordon et al. |
| 7,758,644 B2 | 7/2010 | Trieu |
| 7,762,998 B2 | 7/2010 | Birk et al. |
| 7,763,028 B2 | 7/2010 | Lim et al. |
| 7,763,080 B2 | 7/2010 | Southworth |
| 7,766,855 B2 | 8/2010 | Miethke |
| 7,771,473 B2 | 8/2010 | Thramann |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,785,351 B2 | 8/2010 | Gordon et al. |
| 7,787,958 B2 | 8/2010 | Stevenson |
| 7,789,914 B2 | 9/2010 | Michelson |
| 7,794,476 B2 | 9/2010 | Wisnewski |
| 7,794,480 B2 | 9/2010 | Gordon et al. |
| 7,799,081 B2 | 9/2010 | McKinley |
| 7,799,082 B2 | 9/2010 | Gordon et al. |
| 7,811,328 B2 | 10/2010 | Molz, IV et al. |
| 7,819,921 B2 | 10/2010 | Grotz |
| 7,824,445 B2 | 11/2010 | Biro et al. |
| 7,828,848 B2 | 11/2010 | Chauvin et al. |
| 7,828,849 B2 | 11/2010 | Lim |
| 7,835,779 B2 | 11/2010 | Anderson et al. |
| 7,837,691 B2 | 11/2010 | Cordes et al. |
| 7,837,734 B2 | 11/2010 | Zucherman et al. |
| 7,846,188 B2 | 12/2010 | Moskowitz et al. |
| 7,846,206 B2 | 12/2010 | Oglaza et al. |
| 7,850,733 B2 | 12/2010 | Baynham et al. |
| 7,862,586 B2 | 1/2011 | Malek |
| 7,867,235 B2 | 1/2011 | Fell et al. |
| 7,875,033 B2 | 1/2011 | Richter et al. |
| 7,875,034 B2 | 1/2011 | Josse et al. |
| 7,875,078 B2 | 1/2011 | Wysocki et al. |
| 7,879,098 B1 | 2/2011 | Simmons, Jr. |
| 7,901,381 B2 | 3/2011 | Birk et al. |
| 7,909,852 B2 | 3/2011 | Boomer et al. |
| 7,909,869 B2 | 3/2011 | Gordon et al. |
| 7,918,844 B2 | 4/2011 | Byrum et al. |
| 7,931,688 B2 | 4/2011 | Landry et al. |
| 7,938,841 B2 | 5/2011 | Sharkawy et al. |
| 7,942,903 B2 | 5/2011 | Moskowitz et al. |
| 7,951,180 B2 | 5/2011 | Moskowitz et al. |
| 7,972,363 B2 | 7/2011 | Moskowitz et al. |
| 7,985,256 B2 | 7/2011 | Grotz et al. |
| 7,985,258 B2 | 7/2011 | Zdeblick et al. |
| 7,988,709 B2 | 8/2011 | Clark et al. |
| 8,002,809 B2 | 8/2011 | Baynham |
| 8,011,308 B2 | 9/2011 | Picchio |
| 8,021,430 B2 | 9/2011 | Michelson |
| 8,025,665 B2 | 9/2011 | Lim et al. |
| 8,034,080 B2 | 10/2011 | Malandain et al. |
| 8,043,299 B2 | 10/2011 | Conway |
| 8,043,338 B2 | 10/2011 | Dant |
| 8,052,723 B2 | 11/2011 | Gordon et al. |
| 8,057,473 B2 | 11/2011 | Orsak et al. |
| 8,057,513 B2 | 11/2011 | Kohm et al. |
| 8,062,375 B2 | 11/2011 | Glerum et al. |
| 8,080,041 B2 | 12/2011 | Boehm, Jr. et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,097,035 B2 | 1/2012 | Glenn et al. |
| 8,105,358 B2 | 1/2012 | Phan |
| 8,105,360 B1 | 1/2012 | Connor |
| 8,105,382 B2 | 1/2012 | Olmos et al. |
| 8,114,158 B2 | 2/2012 | Carl et al. |
| 8,118,870 B2 | 2/2012 | Gordon et al. |
| 8,118,871 B2 | 2/2012 | Gordon et al. |
| 8,123,805 B2 | 2/2012 | Makower et al. |
| 8,123,810 B2 | 2/2012 | Gordon et al. |
| 8,128,700 B2 | 3/2012 | Delurio et al. |
| 8,133,280 B2 | 3/2012 | Voellmicke et al. |
| 8,147,549 B2 | 4/2012 | Metcalf, Jr. et al. |
| 8,147,550 B2 | 4/2012 | Gordon et al. |
| 8,162,897 B2 | 4/2012 | Byrum |
| 8,162,979 B2 | 4/2012 | Sachs et al. |
| 8,172,903 B2 | 5/2012 | Gordon et al. |
| 8,177,789 B2 | 5/2012 | Magill et al. |
| 8,187,332 B2 | 5/2012 | McLuen |
| 8,197,490 B2 | 6/2012 | Pool et al. |
| 8,211,149 B2 | 7/2012 | Justis |
| 8,211,151 B2 | 7/2012 | Schwab et al. |
| 8,216,314 B2 | 7/2012 | Richelsoph |
| 8,221,420 B2 | 7/2012 | Keller |
| 8,221,501 B2 | 7/2012 | Eisermann et al. |
| 8,221,502 B2 | 7/2012 | Branch, Jr. |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,257,370 B2 | 9/2012 | Moskowitz et al. |
| 8,257,440 B2 | 9/2012 | Gordon et al. |
| 8,262,666 B2 | 9/2012 | Baynham et al. |
| 8,262,736 B2 | 9/2012 | Michelson |
| 8,267,966 B2 | 9/2012 | McCormack et al. |
| 8,267,969 B2 | 9/2012 | Altarac et al. |
| 8,273,129 B2 | 9/2012 | Baynham et al. |
| 8,278,941 B2 | 10/2012 | Kroh et al. |
| 8,282,671 B2 | 10/2012 | Connor |
| 8,303,601 B2 | 11/2012 | Bandeira et al. |
| 8,303,658 B2 | 11/2012 | Peterman |
| 8,308,804 B2 | 11/2012 | Krueger |
| 8,317,025 B1 | 11/2012 | Kolozs et al. |
| 8,317,866 B2 | 11/2012 | Palmatier et al. |
| 8,323,290 B2 | 12/2012 | Metzger et al. |
| 8,328,818 B1 | 12/2012 | Seifert et al. |
| 8,337,562 B2 | 12/2012 | Landry et al. |
| 8,353,913 B2 | 1/2013 | Moskowitz et al. |
| 8,357,182 B2 | 1/2013 | Seme |
| 8,361,152 B2 | 1/2013 | McCormack et al. |
| 8,366,628 B2 | 2/2013 | Denker et al. |
| 8,366,777 B2 * | 2/2013 | Matthis ............... A61F 2/4465 623/17.11 |
| 8,372,078 B2 | 2/2013 | Collazo |
| 8,377,071 B2 | 2/2013 | Lim et al. |
| 8,382,842 B2 | 2/2013 | Greenhalgh et al. |
| 8,386,018 B2 | 2/2013 | Stauch et al. |
| 8,394,124 B2 | 3/2013 | Biyani |
| 8,398,713 B2 | 3/2013 | Weiman |
| 8,403,958 B2 | 3/2013 | Schwab |
| 8,403,990 B2 | 3/2013 | Dryer et al. |
| 8,414,584 B2 | 4/2013 | Brigido |
| 8,419,795 B2 | 4/2013 | Sweeney |
| 8,425,558 B2 | 4/2013 | McCormack et al. |
| 8,425,608 B2 | 4/2013 | Dewey et al. |
| 8,435,268 B2 | 5/2013 | Thompson et al. |
| 8,435,298 B2 | 5/2013 | Weiman |
| 8,435,299 B2 | 5/2013 | Chauvin et al. |
| 8,439,926 B2 | 5/2013 | Bojarski et al. |
| 8,444,693 B2 | 5/2013 | Reiley |
| 8,444,696 B2 | 5/2013 | Michelson |
| 8,444,697 B1 | 5/2013 | Butler et al. |
| 8,460,389 B2 | 6/2013 | DeLurio et al. |
| 8,469,908 B2 | 6/2013 | Asfora |
| 8,470,004 B2 | 6/2013 | Reiley |
| 8,480,748 B2 | 7/2013 | Poulos |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,491,657 B2 | 7/2013 | Attia et al. |
| 8,494,805 B2 | 7/2013 | Roche et al. |
| 8,496,662 B2 | 7/2013 | Novak et al. |

(56) References Cited

U.S. PATENT DOCUMENTS

| | | |
|---|---|---|
| 8,496,706 B2 | 7/2013 | Ragab et al. |
| 8,506,635 B2 | 8/2013 | Palmatier et al. |
| 8,512,348 B2 | 8/2013 | Chabansky et al. |
| 8,512,407 B2 | 8/2013 | Butler et al. |
| 8,518,062 B2 | 8/2013 | Cole et al. |
| 8,518,114 B2 | 8/2013 | Marik |
| 8,518,120 B2 | 8/2013 | Glerum et al. |
| 8,523,866 B2 | 9/2013 | Sidebotham et al. |
| 8,523,946 B1 | 9/2013 | Swann |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,545,567 B1 | 10/2013 | Krueger |
| 8,556,901 B2 | 10/2013 | Anthony et al. |
| 8,556,911 B2 | 10/2013 | Mehta et al. |
| 8,556,975 B2 | 10/2013 | Lechoslaw et al. |
| 8,556,979 B2 | 10/2013 | Glerum et al. |
| 8,562,653 B2 | 10/2013 | Alamin et al. |
| 8,562,683 B2 | 10/2013 | McKinley |
| 8,568,457 B2 | 10/2013 | Hunziker |
| 8,568,481 B2 | 10/2013 | Olmos et al. |
| 8,617,220 B2 | 10/2013 | Skaggs |
| 8,574,300 B2 | 11/2013 | McManus et al. |
| 8,579,907 B2 | 11/2013 | Lim et al. |
| 8,579,979 B2 | 11/2013 | Edie et al. |
| 8,579,980 B2 | 11/2013 | DeLurio et al. |
| 8,579,981 B2 | 11/2013 | Lim et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,597,360 B2 | 12/2013 | McLuen et al. |
| 8,603,168 B2 | 12/2013 | Gordon et al. |
| 8,613,758 B2 | 12/2013 | Linares |
| 8,623,036 B2 | 1/2014 | Harrison et al. |
| 8,623,054 B2 | 1/2014 | McCormack et al. |
| 8,623,091 B2 | 1/2014 | Suedkamp et al. |
| 8,628,578 B2 | 1/2014 | Miller et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,641,767 B2 | 2/2014 | Landry et al. |
| 8,641,769 B2 | 2/2014 | Malandain |
| 8,647,386 B2 | 2/2014 | Gordon et al. |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,685,095 B2 | 4/2014 | Miller et al. |
| 8,696,720 B2 | 4/2014 | Lazarof |
| 8,702,798 B2 | 4/2014 | Matthis et al. |
| 8,709,086 B2 | 4/2014 | Glerum |
| 8,709,090 B2 | 4/2014 | Makower et al. |
| 8,734,516 B2 | 5/2014 | Moskowitz et al. |
| 8,747,444 B2 | 6/2014 | Moskowitz et al. |
| 8,753,345 B2 | 6/2014 | McCormack et al. |
| 8,753,347 B2 | 6/2014 | McCormack et al. |
| 8,753,377 B2 | 6/2014 | McCormack et al. |
| 8,753,398 B2 | 6/2014 | Gordon et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,778,025 B2 | 7/2014 | Ragab et al. |
| 8,784,450 B2 | 7/2014 | Moskowitz et al. |
| 8,790,343 B2 | 7/2014 | McClellan et al. |
| 8,790,407 B2 | 7/2014 | Chauvin et al. |
| 8,790,409 B2 | 7/2014 | Van den Heuvel et al. |
| 8,795,366 B2 | 8/2014 | Varela |
| 8,828,058 B2 | 9/2014 | Elsebaie et al. |
| 8,828,062 B2 | 9/2014 | McCormack et al. |
| 8,828,066 B2 | 9/2014 | Lazarof |
| 8,828,087 B2 | 9/2014 | Stone et al. |
| 8,834,472 B2 | 9/2014 | McCormack et al. |
| 8,840,651 B2 | 9/2014 | Reiley |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,858,638 B2 | 10/2014 | Michelson |
| 8,864,833 B2 | 10/2014 | Glerum et al. |
| 8,870,881 B2 | 10/2014 | Rezach et al. |
| 8,870,959 B2 | 10/2014 | Arnin |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,708 B2 | 11/2014 | Thalgott et al. |
| 8,894,711 B2 | 11/2014 | Varela |
| 8,894,712 B2 | 11/2014 | Varela |
| 8,906,099 B2 | 12/2014 | Poulos |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,920,507 B2 | 12/2014 | Malandain |
| 8,926,701 B2 | 1/2015 | De Lurio et al. |
| 8,926,704 B2 | 1/2015 | Glerum et al. |
| 8,940,048 B2 | 1/2015 | Butler et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,968,406 B2 | 3/2015 | Arnin |
| 8,968,408 B2 | 3/2015 | Schaller et al. |
| 8,974,534 B2 | 3/2015 | Krueger |
| 8,986,389 B2 | 3/2015 | Lim et al. |
| 8,992,527 B2 | 3/2015 | Guichet |
| 8,992,621 B2 | 3/2015 | Chauvin et al. |
| 8,998,992 B2 | 4/2015 | Seifert et al. |
| 9,005,293 B2 | 4/2015 | Moskowitz et al. |
| 9,011,492 B2 | 4/2015 | McCormack et al. |
| 9,022,917 B2 | 5/2015 | Kasic et al. |
| 9,034,040 B2 | 5/2015 | Seifert et al. |
| 9,034,041 B2 | 5/2015 | Wolters et al. |
| 9,039,771 B2 | 5/2015 | Glerum et al. |
| 9,044,218 B2 | 6/2015 | Young |
| 9,055,985 B2 | 6/2015 | Lazarof |
| 9,060,810 B2 | 6/2015 | Kercher et al. |
| 9,078,703 B2 | 7/2015 | Arbin |
| 9,078,769 B2 | 7/2015 | Farin |
| 9,095,446 B2 | 8/2015 | Landry et al. |
| 9,101,488 B2 | 8/2015 | Malandain |
| 9,119,730 B2 | 9/2015 | Glerum et al. |
| 9,125,757 B2 | 9/2015 | Weiman |
| 9,138,277 B2 | 9/2015 | Fitzpatrick |
| 9,149,364 B2 | 10/2015 | McManus et al. |
| 9,180,017 B2 | 11/2015 | Poulos |
| 9,186,262 B2 | 11/2015 | McLuen et al. |
| 9,192,484 B2 | 11/2015 | Landry et al. |
| 9,204,974 B2 | 12/2015 | Glerum et al. |
| 9,211,196 B2 | 12/2015 | Glerum et al. |
| 9,216,095 B2 | 12/2015 | Glerum et al. |
| 9,233,007 B2 | 1/2016 | Sungarian et al. |
| 9,271,846 B2 | 3/2016 | Lim et al. |
| 9,283,089 B2 | 3/2016 | McKay |
| 9,301,854 B2 | 4/2016 | Moskowitz et al. |
| 9,320,610 B2 | 4/2016 | Alheidt et al. |
| 9,320,615 B2 | 4/2016 | Suedkamp et al. |
| 9,351,848 B2 | 5/2016 | Glerum et al. |
| 9,358,123 B2 | 6/2016 | McLuen et al. |
| 9,358,126 B2 | 6/2016 | Glerum et al. |
| 9,358,128 B2 | 6/2016 | Glerum et al. |
| 9,358,129 B2 | 6/2016 | Weiman |
| 9,398,961 B2 | 7/2016 | Malandain |
| 9,402,739 B2 | 8/2016 | Weiman et al. |
| 9,408,707 B2 | 8/2016 | Oglaza et al. |
| 9,408,708 B2 | 8/2016 | Greenhalgh |
| 9,414,936 B2 | 8/2016 | Miller et al. |
| 9,445,856 B2 | 9/2016 | Seifert et al. |
| 9,445,919 B2 | 9/2016 | Palmatier et al. |

(56) References Cited

U.S. PATENT DOCUMENTS

| | | |
|---|---|---|
| 9,452,063 B2 | 9/2016 | Glerum et al. |
| 9,486,324 B2 | 11/2016 | Hochschuler et al. |
| 9,486,328 B2 | 11/2016 | Jimenez et al. |
| 9,492,287 B2 | 11/2016 | Glerum et al. |
| 9,492,288 B2 | 11/2016 | Wagner ............... A61F 2/4611 |
| 9,510,954 B2 | 12/2016 | Glerum et al. |
| 9,510,955 B2 | 12/2016 | Marino et al. |
| 9,526,627 B2 | 12/2016 | Tabor et al. |
| 9,526,628 B2 | 12/2016 | Krueger |
| 9,532,821 B2 | 1/2017 | Moskowitz et al. |
| 9,539,108 B2 | 1/2017 | Glerum et al. |
| 9,545,319 B2 | 1/2017 | Farin |
| 9,549,824 B2 | 1/2017 | McAfee |
| 9,566,168 B2 | 2/2017 | Glerum et al. |
| 9,579,124 B2 | 2/2017 | Gordon et al. |
| 9,579,215 B2 | 2/2017 | Suedkamp et al. |
| 9,585,767 B2 | 3/2017 | Robinson |
| 9,592,131 B2 | 3/2017 | Sandstrom et al. |
| 9,597,200 B2 | 3/2017 | Glerum et al. |
| 9,603,713 B2 | 3/2017 | Moskowitz et al. |
| 9,622,791 B2 | 4/2017 | McCormack et al. |
| 9,622,875 B2 | 4/2017 | Moskowitz et al. |
| 9,629,665 B2 | 4/2017 | McCormack et al. |
| 9,642,712 B2 | 5/2017 | Schaller et al. |
| 9,655,747 B2 | 5/2017 | Glerum et al. |
| 9,662,223 B2 | 5/2017 | Matthis et al. |
| 9,675,385 B2 | 6/2017 | Moskowitz et al. |
| 9,675,469 B2 | 6/2017 | Landry et al. |
| 9,730,802 B1 | 8/2017 | Harvey |
| 9,801,734 B1 | 10/2017 | Stein et al. |
| 9,937,053 B2 | 4/2018 | Melkent et al. |
| 9,962,272 B1 | 5/2018 | Daffinson et al. |
| 10,492,924 B2 | 12/2019 | Stein et al. |
| 2002/0040243 A1 | 4/2002 | Attali et al. |
| 2002/0045945 A1 | 4/2002 | Liu et al. |
| 2002/0050112 A1 | 5/2002 | Koch et al. |
| 2002/0068976 A1 | 6/2002 | Jackson ............... A61F 2/447 623/17.15 |
| 2002/0072758 A1 | 6/2002 | Reo et al. |
| 2002/0161444 A1 | 10/2002 | Choi |
| 2002/0164905 A1 | 11/2002 | Bryant |
| 2002/0165613 A1 | 11/2002 | Lin et al. |
| 2003/0040671 A1 | 2/2003 | Somogyi et al. |
| 2003/0135279 A1 | 7/2003 | Michelson |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0087947 A1 | 5/2004 | Lim et al. |
| 2004/0133219 A1 | 7/2004 | Forsell |
| 2004/0133280 A1 | 7/2004 | Trieu |
| 2004/0138725 A1 | 7/2004 | Forsell |
| 2004/0193266 A1 | 9/2004 | Meyer |
| 2004/0254643 A1 | 12/2004 | Jackson |
| 2005/0034705 A1 | 2/2005 | McClendon |
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0107878 A1 | 5/2005 | Conchy |
| 2005/0159754 A1 | 7/2005 | Odrich |
| 2005/0171541 A1 | 8/2005 | Boehm, Jr. et al. |
| 2005/0192669 A1 | 9/2005 | Zdeblick et al. |
| 2005/0203625 A1 | 9/2005 | Boehm, Jr. et al. |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2005/0278036 A1 | 12/2005 | Leonard et al. |
| 2005/0283245 A1 | 12/2005 | Gordon et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069436 A1 | 3/2006 | Sutton et al. |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0095136 A1 | 5/2006 | McLuen |
| 2006/0122701 A1 | 6/2006 | Kiester |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0195192 A1 | 8/2006 | Gordon et al. |
| 2006/0200134 A1 | 9/2006 | Freid et al. |
| 2006/0204156 A1 | 9/2006 | Takehara et al. |
| 2006/0229729 A1 | 10/2006 | Gordon et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241764 A1 | 10/2006 | Michelson |
| 2006/0241767 A1 | 10/2006 | Doty |
| 2006/0241774 A1 | 10/2006 | Attali et al. |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0073406 A1 | 3/2007 | Gordon et al. |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0270954 A1 | 11/2007 | Wu |
| 2007/0270963 A1 | 11/2007 | Melkent et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021559 A1 | 1/2008 | Thramann |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0051902 A1 | 2/2008 | Dwyer |
| 2008/0065219 A1 | 3/2008 | Dye |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0147193 A1 | 6/2008 | Matthis ............... A61F 2/4465 623/17.16 |
| 2008/0161933 A1 | 7/2008 | Grotz et al. |
| 2008/0167685 A1 | 7/2008 | Allard et al. |
| 2008/0172063 A1 | 7/2008 | Taylor |

(56) References Cited

U.S. PATENT DOCUMENTS

| | | |
|---|---|---|
| 2008/0177319 A1 | 7/2008 | Schwab |
| 2008/0177326 A1 | 7/2008 | Thompson |
| 2008/0183204 A1 | 7/2008 | Greenhalgh et al. |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0043394 A1 | 2/2009 | Zdeblick et al. |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0198241 A1 | 8/2009 | Phan |
| 2009/0198245 A1 | 8/2009 | Phan |
| 2009/0198338 A1 | 8/2009 | Phan |
| 2009/0216113 A1 | 8/2009 | Meier et al. |
| 2009/0275984 A1 | 11/2009 | Kim et al. |
| 2009/0299478 A1 | 12/2009 | Carls et al. |
| 2010/0004654 A1 | 1/2010 | Schmitz et al. |
| 2010/0023057 A1 | 1/2010 | Aeschlimann et al. |
| 2010/0049325 A1 | 2/2010 | Biedermann et al. |
| 2010/0057127 A1 | 3/2010 | McGuire et al. |
| 2010/0070041 A1 | 3/2010 | Peterman et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0152853 A1 | 6/2010 | Kirschman |
| 2010/0168751 A1 | 7/2010 | Anderson et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234952 A1 | 9/2010 | Peterman |
| 2010/0241231 A1 | 9/2010 | Marino et al. |
| 2010/0249782 A1 | 9/2010 | Durham |
| 2010/0249933 A1 | 9/2010 | Trieu |
| 2010/0256626 A1 | 10/2010 | Muller et al. |
| 2010/0262239 A1 | 10/2010 | Boyden et al. |
| 2010/0286780 A1 | 11/2010 | Dryer et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0015742 A1 | 1/2011 | Hong |
| 2011/0029086 A1 | 2/2011 | Glazer et al. |
| 2011/0057756 A1 | 3/2011 | Marinescu et al. |
| 2011/0066188 A1 | 3/2011 | Seme et al. |
| 2011/0098748 A1 | 4/2011 | Jangra |
| 2011/0137349 A1 | 6/2011 | Moskowitz et al. |
| 2011/0144755 A1 | 6/2011 | Baynham et al. |
| 2011/0152725 A1 | 6/2011 | Demir et al. |
| 2011/0172774 A1 | 7/2011 | Varela ............... A61F 2/447 623/17.16 |
| 2011/0196435 A1 | 8/2011 | Forsell |
| 2011/0202138 A1 | 8/2011 | Shenoy et al. |
| 2011/0208312 A1 | 8/2011 | Moskowitz et al. |
| 2011/0218627 A1 | 9/2011 | Rampersaud et al. |
| 2011/0238126 A1 | 9/2011 | Soubeiran |
| 2011/0238184 A1 | 9/2011 | Zdeblick et al. |
| 2011/0257655 A1 | 10/2011 | Copf, Jr. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0058451 A1 | 3/2012 | Lazarof |
| 2012/0059472 A1 | 3/2012 | Weiman |
| 2012/0059481 A1 | 3/2012 | Abernathie et al. |
| 2012/0088953 A1 | 4/2012 | King |
| 2012/0109207 A1 | 5/2012 | Trieu |
| 2012/0109319 A1 | 5/2012 | Perisic |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0197405 A1 | 8/2012 | Cuevas et al. |
| 2012/0221106 A1 | 8/2012 | Makower et al. |
| 2012/0245691 A1 | 9/2012 | Reimels |
| 2012/0271353 A1 | 10/2012 | Barry |
| 2012/0277861 A1 | 11/2012 | Steele et al. |
| 2012/0296234 A1 | 11/2012 | Wilhelm et al. |
| 2012/0329882 A1 | 12/2012 | Messersmith et al. |
| 2012/0330419 A1 | 12/2012 | Moskowitz et al. |
| 2012/0330421 A1 | 12/2012 | Weiman |
| 2013/0013066 A1 | 1/2013 | Landry et al. |
| 2013/0013070 A1 | 1/2013 | McCormack et al. |
| 2013/0018468 A1 | 1/2013 | Moskowitz et al. |
| 2013/0018469 A1 | 1/2013 | Moskowitz et al. |
| 2013/0023991 A1 | 1/2013 | Moskowitz et al. |
| 2013/0023992 A1 | 1/2013 | Moskowitz et al. |
| 2013/0053962 A1 | 2/2013 | Moskowitz et al. |
| 2013/0072932 A1 | 3/2013 | Stauch |
| 2013/0103153 A1 | 4/2013 | Blackwell et al. |
| 2013/0103154 A1 | 4/2013 | Trieu et al. |
| 2013/0110168 A1 | 5/2013 | McCormack et al. |
| 2013/0110248 A1 | 5/2013 | Zipnick |
| 2013/0116791 A1 | 5/2013 | Theofilos |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0144388 A1 | 6/2013 | Emery et al. |
| 2013/0150863 A1 | 6/2013 | Baumgartner |
| 2013/0150889 A1 | 6/2013 | Fening et al. |
| 2013/0158669 A1 | 6/2013 | Sungarian et al. |
| 2013/0178903 A1 | 7/2013 | Abdou |
| 2013/0178940 A1 | 7/2013 | Farley |
| 2013/0204371 A1 | 8/2013 | McLuen et al. |
| 2013/0211521 A1 | 8/2013 | Shenoy et al. |
| 2013/0211525 A1 | 8/2013 | McLuen et al. |
| 2013/0231747 A1 | 9/2013 | Olmos et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0297028 A1 | 11/2013 | Zipnick |
| 2013/0297029 A1 | 11/2013 | Kana et al. |
| 2013/0310935 A1 | 11/2013 | Swann |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0107790 A1 | 4/2014 | Combrowski |
| 2014/0128920 A1 | 5/2014 | Kantelbardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0249629 A1 | 9/2014 | Moskowitz et al. |
| 2014/0257412 A1 | 9/2014 | Patty et al. |
| 2014/0277446 A1 | 9/2014 | Clifford et al. |
| 2014/0296916 A1 | 10/2014 | McCormack et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0081021 A1 | 3/2015 | Ciupik |
| 2015/0094814 A1 | 4/2015 | Emerick et al. |

(56) References Cited

U.S. PATENT DOCUMENTS

| | | |
|---|---|---|
| 2015/0105782 A1 | 4/2015 | D'Lima et al. |
| 2015/0105824 A1 | 4/2015 | Moskowitz et al. |
| 2015/0216518 A1 | 8/2015 | McCormack et al. |
| 2015/0230931 A1 | 8/2015 | Greenhalgh |
| 2015/0230934 A1 | 8/2015 | Chauvin et al. |
| 2015/0351925 A1 | 12/2015 | Emerick et al. |
| 2015/0374507 A1 | 12/2015 | Wolters et al. |
| 2016/0008040 A1 | 1/2016 | McCormack et al. |
| 2016/0015527 A1 | 1/2016 | McManus et al. |
| 2016/0015529 A1 | 1/2016 | Reimels |
| 2016/0030191 A1 | 2/2016 | McLuen et al. |
| 2016/0058579 A1 | 3/2016 | Aeschlimann et al. |
| 2016/0089247 A1 | 3/2016 | Nichols et al. |
| 2016/0120660 A1 | 5/2016 | Melkent et al. |
| 2016/0135961 A1 | 5/2016 | Aeschlimann et al. |
| 2016/0143748 A1 | 5/2016 | Lim et al. |
| 2016/0151168 A1 | 6/2016 | Weiman .................. A61F 2/44 623/17.16 |
| 2016/0166396 A1 | 6/2016 | McClintock |
| 2016/0193056 A1 | 7/2016 | McKay |
| 2016/0213482 A1 | 7/2016 | Alheidt et al. |
| 2016/0242932 A1 | 8/2016 | McLuen et al. |
| 2016/0296340 A1 | 10/2016 | Gordon et al. |
| 2016/0302943 A1 | 10/2016 | Oglaza et al. |
| 2016/0310291 A1 | 10/2016 | Greenhalgh |
| 2016/0317315 A1 | 11/2016 | Weiman |
| 2016/0324659 A1 | 11/2016 | Malandain |
| 2016/0324661 A1 | 11/2016 | Miller et al. |
| 2016/0354131 A1 | 12/2016 | Seifert et al. |
| 2016/0374826 A1 | 12/2016 | Palmatier et al. |
| 2016/0374830 A1 | 12/2016 | Moskowitz et al. |
| 2017/0035468 A1 | 2/2017 | McCormack et al. |
| 2017/0035576 A1 | 2/2017 | Schaller et al. |
| 2017/0086986 A1 | 3/2017 | McAfee |
| 2017/0100255 A1 | 4/2017 | Hleihil et al. |
| 2017/0119539 A1 | 5/2017 | Glerum et al. |
| 2017/0119540 A1 | 5/2017 | Greenhalgh |
| 2017/0119541 A1 | 5/2017 | Greenhalgh |
| 2017/0119542 A1 | 5/2017 | Logan et al. |
| 2017/0119546 A1 | 5/2017 | Farin |
| 2017/0128229 A1 | 5/2017 | Suedkamp et al. |
| 2017/0165083 A1 | 6/2017 | Greenhalgh |

FOREIGN PATENT DOCUMENTS

| | | |
|---|---|---|
| AU | 2011203582 | 8/2011 |
| CA | 1337842 | 1/1996 |
| CA | 2447257 | 12/1996 |
| CN | 2668075 | 1/2005 |
| CN | 1621015 | 6/2005 |
| CN | 2730336 | 10/2005 |
| CN | 1697630 A | 11/2005 |
| CN | 201861800 | 4/2006 |
| CN | 101040807 A | 9/2007 |
| CN | 101268963 | 9/2008 |
| CN | 202191381 | 4/2012 |
| CN | 202235781 | 5/2012 |
| CN | 203001182 | 6/2013 |
| CN | 103356310 | 10/2013 |
| DE | 1541262 A1 | 6/1969 |
| DE | 8515687 U1 | 12/1985 |
| DE | 4012622 | 7/1991 |
| DE | 4416605 | 6/1995 |
| DE | 19626230 A1 | 1/1998 |
| DE | 19745654 A1 | 4/1999 |
| DE | 10241948 | 4/2004 |
| DE | 102005033608 | 1/2007 |
| DE | 102005045070 A1 | 4/2007 |
| DE | 102010004133 | 9/2011 |
| DE | 102012203256 | 9/2013 |
| EP | 0635246 | 1/1995 |
| EP | 0663184 A1 | 7/1995 |
| EP | 0880950 | 12/1998 |
| EP | 1290985 | 3/2003 |
| EP | 1382315 | 1/2004 |
| EP | 1532949 | 5/2005 |
| EP | 1541096 | 6/2005 |
| EP | 1889587 | 2/2008 |
| EP | 1905388 A1 | 4/2008 |
| EP | 2213263 | 8/2010 |
| EP | 2226039 | 9/2010 |
| EP | 2510904 | 10/2012 |
| ES | 2067421 | 3/1995 |
| ES | 2099008 | 5/1997 |
| FR | 2707477 | 1/1995 |
| FR | 2708192 | 2/1995 |
| FR | 2717068 | 9/1995 |
| FR | 2803741 | 7/2001 |
| FR | 2815845 | 5/2002 |
| FR | 2866228 | 8/2005 |
| FR | 2866229 | 8/2005 |
| FR | 2874814 | 3/2006 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2943529 | 10/2010 |
| FR | 2943530 | 10/2010 |
| FR | 2961386 B1 | 12/2011 |
| FR | 2981261 | 4/2013 |
| JP | H0956736 | 3/1997 |
| JP | 2002500063 A | 1/2002 |
| JP | 2005137418 | 6/2005 |
| JP | 2008054710 | 3/2008 |
| JP | 2008126085 | 6/2008 |
| KR | 20010112139 | 12/2001 |
| KR | 20020025647 | 4/2002 |
| KR | 100410823 | 1/2003 |
| KR | 20030012142 | 2/2003 |
| KR | 20040064577 | 7/2004 |
| KR | 20050064501 | 6/2005 |
| KR | 20080001064 | 1/2008 |
| KR | 20080042341 | 5/2008 |
| KR | 100953930 | 4/2010 |
| KR | 20120119812 | 10/2012 |
| KR | 20130082281 | 7/2013 |
| RU | 2063730 | 7/1996 |
| RU | 2210343 | 8/2003 |
| RU | 105157 | 6/2011 |
| RU | 2460499 | 9/2012 |
| RU | 131611 | 8/2013 |
| SU | 988281 | 1/1983 |
| SU | 1424826 | 9/1988 |
| WO | WO9000037 | 1/1990 |
| WO | WO9531158 | 11/1995 |
| WO | WO9700054 | 1/1997 |
| WO | WO1998044858 A1 | 10/1998 |
| WO | WO9926562 | 6/1999 |
| WO | WO1999051160 A1 | 10/1999 |
| WO | WO200074605 | 12/2000 |
| WO | WO2001024697 A1 | 4/2001 |
| WO | WO2001045485 A3 | 6/2001 |
| WO | WO2001045487 A2 | 6/2001 |
| WO | WO2001067973 A2 | 9/2001 |
| WO | WO2001078614 A1 | 10/2001 |
| WO | WO200392507 | 11/2003 |
| WO | WO2004012634 | 2/2004 |
| WO | WO2006081843 | 8/2006 |
| WO | WO2006117463 | 11/2006 |
| WO | WO2006134262 | 12/2006 |
| WO | WO2007009107 | 1/2007 |
| WO | WO2007013059 A3 | 2/2007 |
| WO | WO2007015239 A3 | 2/2007 |
| WO | WO2007028706 | 3/2007 |
| WO | WO2008132322 | 11/2008 |
| WO | WO2009064787 | 5/2009 |
| WO | WO2010148112 | 12/2010 |
| WO | WO2011116158 A3 | 9/2011 |
| WO | WO2011142761 | 11/2011 |
| WO | WO2012031267 | 3/2012 |
| WO | WO2013119528 A1 | 8/2013 |

(56) References Cited

FOREIGN PATENT DOCUMENTS

| WO | WO2013152257 | 10/2013 |
|---|---|---|
| WO | WO2014040013 A1 | 3/2014 |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.
Amer et al., "Evaluation of treatment of late-onset tibia vara using gradual angulation translation high tibial osteotomy", ACTA Orthopaedica Belgica, 2010, pp. 360-366, 76, No. 3.
Angrisani et al., "Lap-Band® Rapid Port™ System: Preliminary results in 21 patients", Obesity Surgery, 2005, p. 936, 15, No. 7.
Baumgart et al., "A fully implantable, programmable distraction nail (Fitbone)—new perspectives for corrective and reconstructive limb surgery.", Practice of Intramedullary Locked Nails, 2006, pp. 189-198.
Baumgart et al., "The bioexpandable prosthesis: A new perspective after resection of malignant bone tumors in children.", J Pediatr Hematol Oncol, 2005, pp. 452-455, 27, No. 8.
Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.
Boudjemline et al., "Off-label use of an adjustable gastric banding system for pulmonary artery banding.", The Journal of Thoracic and Cardiovascular Surgery, 2006, pp. 1130-1135, 131, No. 5.
Brown et al., "Single port surgery and the Dundee Endocone.", SAGES Annual Scientific Sessions: Emerging Technology Poster Abstracts, 2007, ETP007, pp. 323-324.
Buchowski et al., "Temporary internal distraction as an aid to correction of severe scoliosis", J Bone Joint Surg Am, 2006, pp. 2035-2041, 88-A, No. 9.
Burghardt et al., "Mechanical failure of the Intramedullary Skeletal Kinetic Distractor in limb lengthening.", J Bone Joint Surg Br, 2011, pp. 639-643, 93-B, No. 5.
Burke, "Design of a minimally invasive non fusion device for the surgical management of scoliosis in the skeletally immature", Studies in Health Technology and Informatics, 2006, pp. 378-384, 123.
Carter et al., "A cumulative damage model for bone fracture.", Journal of Orthopaedic Research, 1985, pp. 84-90, 3, No. 1.
Chapman et al., "Laparoscopic adjustable gastric banding in the treatment of obesity: A systematic literature review.", Surgery, 2004, pp. 326-351, 135, No. 3.
Cole et al., "Operative technique intramedullary skeletal kinetic distractor: Tibial surgical technique.", Orthofix, 2005.
Cole et al., "The intramedullary skeletal kinetic distractor (ISKD): first clinical results of a new intramedullary nail for lengthening of the femur and tibia.", Injury, 2001, pp. S-D-129-S-D-139, 32.
Dailey et al., "A novel intramedullary nail for micromotion stimulation of tibial fractures.", Clinical Biomechanics, 2012, pp. 182-188, 27, No. 2.
Daniels et al., "A new method for continuous intraoperative measurement of Harrington rod loading patterns.", Annals of Biomedical Engineering, 1984, pp. 233-246, 12, No. 3.
De Giorgi et al., "Cotrel-Dubousset instrumentation for the treatment of severe scoliosis.", European Spine Journal, 1999, pp. 8-15, No. 1.
Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.

Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.
Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. SI05-SI15, No. 355S.
Grass et al., "Intermittent distracting rod for correction of high neurologic risk congenital scoliosis.", Spine, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Horbach et al., "First experiences with the routine use of the Rapid Port™ system with the Lap-Band®.", Obesity Surgery, 2006, p. 418, 16, No. 4.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
Invis®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.

(56) References Cited

OTHER PUBLICATIONS

Kent et al.. "Assessment and correction of femoral malrotation following intramedullary nailing of the femur.", Acta Orthop Belg, 2010, pp. 580-584, 76, No. 5.

Klemme et al., "Spinal instrumentation without fusion for progressive scoliosis in young children", Journal of Pediatric Orthopaedics. 1997, pp. 734-742, 17, No. 6.

Korenkov et al., "Port function after laparoscopic adjustable gastric banding for morbid obesity.", Surgical Endoscopy, 2003, pp. 1068-1071, 17, No. 7.

Krieg et al., "Leg lengthening with a motorized nail in adolescents.", Clinical Orthopaedics and Related Research, 2008, pp. 189-197, 466, No. 1.

Kucukkaya et al., "The new intramedullary cable bone transport technique.", Journal of Orthopaedic Trauma, 2009, pp. 531-536, 23, No. 7.

Lechner et al., "In vivo band manometry: A new method in band adjustment", Obesity Surgery, 2005, p. 935, 15, No. 7.

Lechner et al., "Intra-band manometry for band adjustments: The basics", Obesity Surgery, 2006, pp. 417-418, 16, No. 4.

Li et al., "Bone transport over an intramedullary nail: A case report with histologic examination of the regenerated segment.", Injury, 1999, pp. 525-534, 30, No. 8.

Lonner, "Emerging minimally invasive technologies for the management of scoliosis.", Orthopedic Clinics of North America, 2007, pp. 431-440, 38, No. 3.

Matthews et al., "Magnetically adjustable intraocular lens.", Journal of Cataract and Refractive Surgery, 2003, pp. 2211-2216, 29, No. 11.

Micromotion, "Micro Drive Engineering • General catalogue.", 2009, pp. 14-24.

Mineiro et al., "Subcutaneous rodding for progressive spinal curvatures: Early results.", Journal of Pediatric Orthopaedics, 2002, pp. 290-295, 22, No. 3.

Moe et al., "Harrington instrumentation without fusion plus external orthotic support for the treatment of difficult curvature problems in young children.", Clinical Orthopaedics and Related Research, 1984, pp. 35-45, 185.

Montague et al., "Magnetic gear dynamics for servo control.", Melecon 2010—2010 15th IEEE Mediterranean Electrotechnical Conference, Valletta, 2010, pp. 1192-1197.

Montague et al., "Servo control of magnetic gears.", IEEE/ASME Transactions on Mechatronics, 2012, pp. 269-278, 17, No. 2.

Nachemson et al., "Intravital wireless telemetry of axial forces in Harrington distraction rods in patients with idiopathic scoliosis.", The Journal of Bone and Joint Surgery, 1971, pp. 445-465, 53, No. 3.

Nachlas et al., "The cure of experimental scoliosis by directed growth control.", The Journal of Bone and Joint Surgery, 1951, pp. 24-34, 33-A, No. 1.

Newton et al., "Fusionless scoliosis correction by anterolateral tethering . . . can it work ?.", 39th Annual Scoliosis Research Society Meeting, 2004.

Oh et al., "Bone transport over an intramedullary nail for reconstruction of long bone defects in tibia.", Archives of Orthopaedic and Trauma Surgery, 2008, pp. 801-808, 128, No. 8.

Ozcivici et al., "Mechanical signals as anabolic agents in bone.", Nature Reviews Rheumatology, 2010, pp. 50-59, 6, No. 1.

Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.

Prontes, "Longest bone in body.", eHow.com, 2012.

Rathjen et al., "Clinical and radiographic results after implant removal in idiopathic scoliosis.", Spine, 2007, pp. 2184-2188, 32, No. 20.

Ren et al., "Laparoscopic adjustable gastric banding: Surgical technique", Journal of Laparoendoscopic & Advanced Surgical Techniques, 2003, pp. 257-263, 13, No. 4.

Reyes-Sanchez et al., "External fixation for dynamic correction of severe scoliosis", The Spine Journal, 2005, pp. 418-426, 5, No. 4.

Rinsky et al., "Segmental instrumentation without fusion in children with progressive scoliosis.", Journal of Pediatric Orthopedics, 1985, pp. 687-690, 5, No. 6.

Rode et al., "A simple way to adjust bands under radiologic control", Obesity Surgery, 2006, p. 418, 16, No. 4.

Schmerling et al., "Using the shape recovery of nitinol in the Harrington rod treatment of scoliosis.", Journal of Biomedical Materials Research, 1976, pp. 879-892, 10, No. 6.

Scott et al., "Transgastric, transcolonic and transvaginal cholecystectomy using magnetically anchored instruments.", Sages Annual Scientific Sessions, Poster Abstracts, Apr. 18-22, 2007, P511, p. 306.

Sharke, "The machinery of life", Mechanical Engineering Magazine, Feb. 2004, Printed from Internet site Oct. 24, 2007 http://www.memagazine.org/contents/current/features/moflife/moflife.html.

Shiha et al., "Ilizarov gradual correction of genu varum deformity in adults.", Acta Orthop Belg, 2009, pp. 784-791, 75, No. 6.

Simpson et al., "Femoral lengthening with the intramedullary skeletal kinetic distractor.", Journal of Bone and Joint Surgery, 2009, pp. 955-961, 91-B, No. 7.

Smith, "The use of growth-sparing instrumentation in pediatric spinal deformity.", Orthopedic Clinics of North America, 2007, pp. 547-552, 38, No. 4.

Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).

Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).

Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.

Sun et al., "Masticatory mechanics of a mandibular distraction osteogenesis site: Interfragmentary micromovement.", Bone, 2007, pp. 188-196, 41, No. 2.

Synthes Spine, "VEPTR II. Vertical Expandable Prosthetic Titanium Rib II: Technique Guide.", 2008, 40 pgs.

Synthes Spine, "VEPTR Vertical Expandable Prosthetic Titanium Rib, Patient Guide.", 2005, 26 pgs.

Takaso et al., "New remote-controlled growing-rod spinal instrumentation possibly applicable for scoliosis in young children.", Journal of Orthopaedic Science, 1998, pp. 336-340, 3, No. 6.

Teli et al., "Measurement of forces generated during distraction of growing rods.", Journal of Children's Orthopaedics, 2007, pp. 257-258, 1, No. 4.

Tello, "Harrington instrumentation without arthrodesis and consecutive distraction program for young children with severe spinal deformities: Experience and technical details.", The Orthopedic Clinics of North America, 1994, pp. 333-351, 25, No. 2.

Thaller et al., "Limb lengthening with fully implantable magnetically actuated mechanical nails (Phenix®)—Preliminary results.", Injury, 2014 (E-published Oct. 28, 2013), pp. S60-S65, 45.

Thompson et al., "Early onset scoliosis: Future directions", 2007, J Bone Joint Surg Am, pp. 163-166, 89-A, Suppl 1.

Thompson et al., "Growing rod techniques in early-onset scoliosis", Journal of Pediatric Orthopedics, 2007, pp. 354-361, 27, No. 3.

Thonse et al., "Limb lengthening with a fully implantable, telescopic, intramedullary nail.", Operative Techniques in Orthopedics, 2005, pp. 355-362, 15, No. 4.

Trias et al., "Dynamic loads experienced in correction of idiopathic scoliosis using two types of Harrington rods.", Spine, 1979, pp. 228-235, 4, No. 3.

Verkerke et al., "An extendable modular endoprosthetic system for bone tumor management in the leg", Journal of Biomedical Engineering, 1990, pp. 91-96, 12, No. 2.

(56) References Cited

OTHER PUBLICATIONS

Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.

Verkerke et al., "Development and test of an extendable endoprosthesis for bone reconstruction in the leg.", The International Journal of Artificial Organs, 1994, pp. 155-162, 17, No. 3.

Weiner et al., "Initial clinical experience with telemetrically adjustable gastric banding", Surgical Technology International, 2005, pp. 63-69, 15.

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.

White, III et al., "The clinical biomechanics of scoliosis.", Clinical Orthopaedics and Related Research, 1976, pp. 100-112, 118.

Yonnet, "A new type of permanent magnet coupling.", IEEE Transactions on Magnetics, 1981, pp. 2991-2993, 17, No. 6.

Yonnet, "Passive magnetic bearings with permanent magnets.", IEEE Transactions on Magnetics, 1978, pp. 803-805, 14, No. 5.

Zheng et al., "Force and torque characteristics for magnetically driven blood pump.", Journal of Magnetism and Magnetic Materials, 2002, pp. 292-302, 241, No. 2.

U.S. Appl. No. 14/285,590, Stein.

\* cited by examiner

LORDOTIC EXPANDABLE INTERBODY IMPLANT AND METHOD OF USING SAME

CROSS REFERENCE TO RELATED APPLICATIONS

This application is a continuation application of U.S. patent application Ser. No. 16/667,766 filed on Oct. 29, 2019, which is a continuation application of U.S. patent application Ser. No. 15/799,554 filed on Oct. 31, 2017, now U.S. Pat. No. 10,492,924, which is a continuation application of U.S. patent application Ser. No. 14/456,640 filed on Aug. 11, 2014, now U.S. Pat. No. 9,801,734, which claims priority to U.S. Provisional Application No. 61/864,132 filed on Aug. 9, 2013, each of which is incorporated by reference in its entirely herein.

BACKGROUND

This application relates to expandable interbody spinal fusion implants and methods of using the same.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary sill in the art having the benefit of this disclosure. The expandable spinal fusion implant and related methods disclosed herein boasts a variety of inventive features and components that warrant patent protection, both individually and in combination.

In general, the expandable spinal fusion implants described in this document include a housing, upper and lower endplates, a translating wedge positioned between the upper and lower endplates and within the housing, and a drive mechanism to drive translation of the wedge. The expandable spinal fusion implant is designed to be inserted into the disc space between adjacent vertebral bodies from a posterior approach. The implant may be made of any suitable, biocompatible material or combination of materials. For example, the implant components may be metal, polyether ether ketone (PEEK), or a combination of the metal and PEEK. The implant is configured to be inserted into the disc space in a collapsed state and upon being seated in a desired location within the disc space the distal end of the implant is expanded in height to create an implant with a lordotic angle (i.e. the anterior height of the implant is greater than the posterior height of the implant, thereby restoring a more natural lordotic curvature of the particular segment of the lumbar spine). The expansion is accomplished by engaging the drive mechanism with a tool to activate the drive mechanism and cause the translating wedge to move between the implants in a distal direction.

Figure 1:
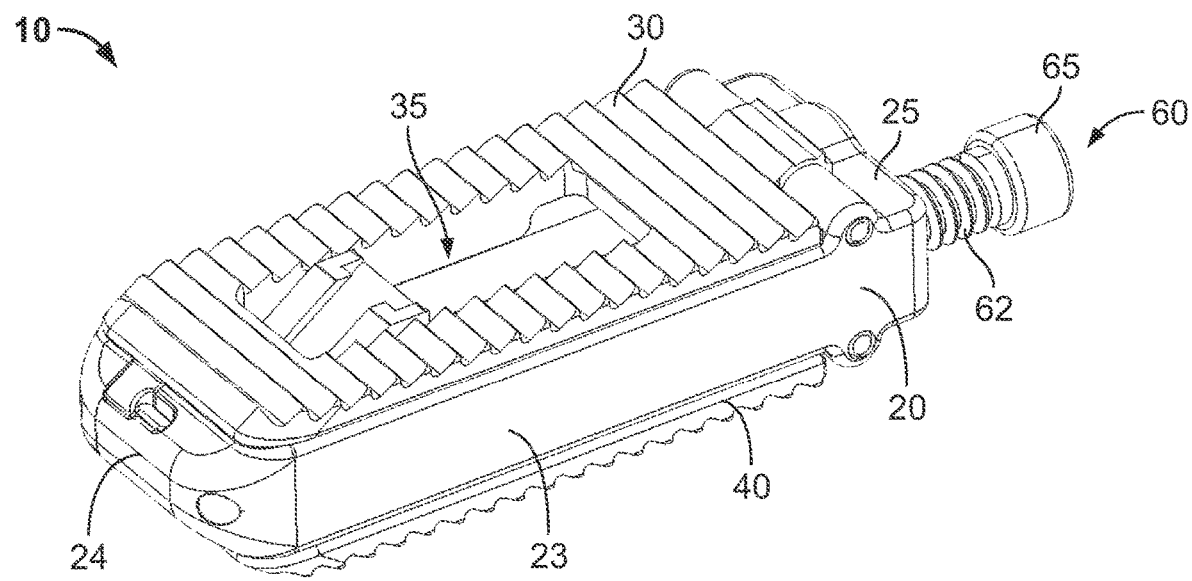
FIG. 1 is a perspective view of an expandable spinal fusion implant in a collapsed position, according to an exemplary embodiment.
Figure 2:
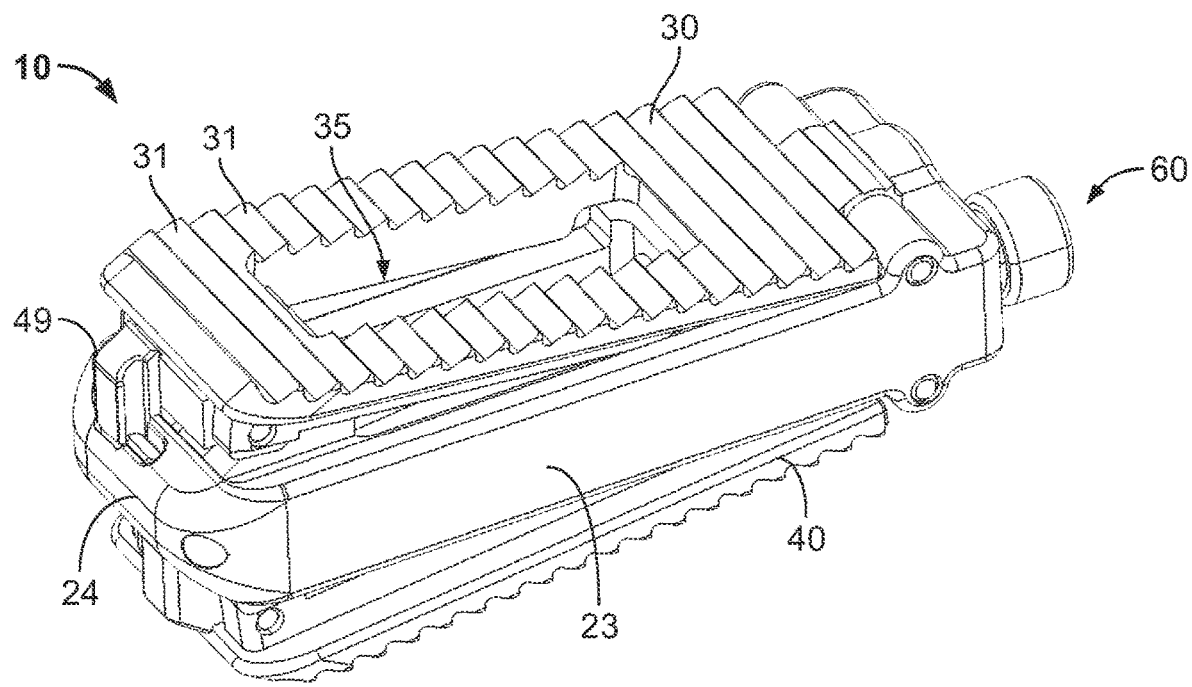
FIG. 2 is a perspective view of the expandable spinal fusion implant of FIG. 1 in an expanded position.
Figure 3:
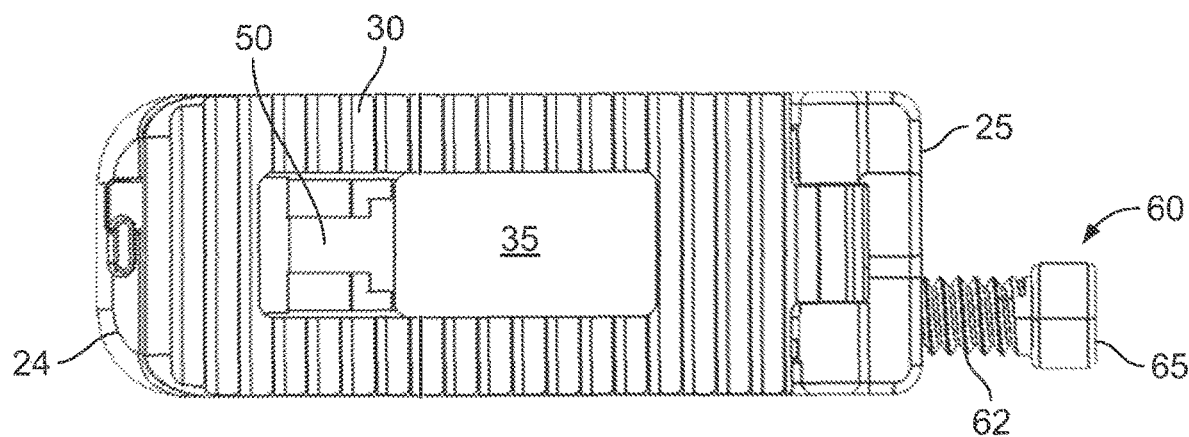
FIG. 3 is a top view of the expandable spinal fusion implant of FIG. 1.
Figure 4:
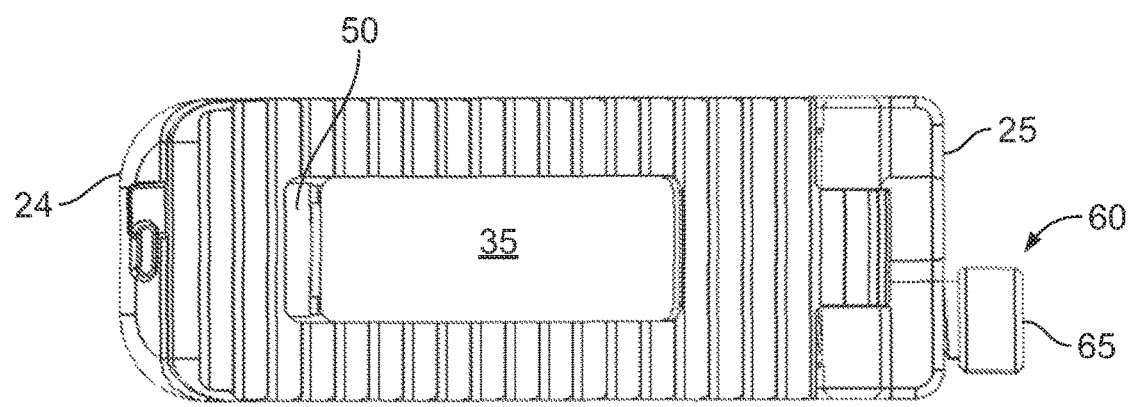
FIG. 4 is a top view of the expandable spinal fusion implant of FIG. 2.
Figure 5:
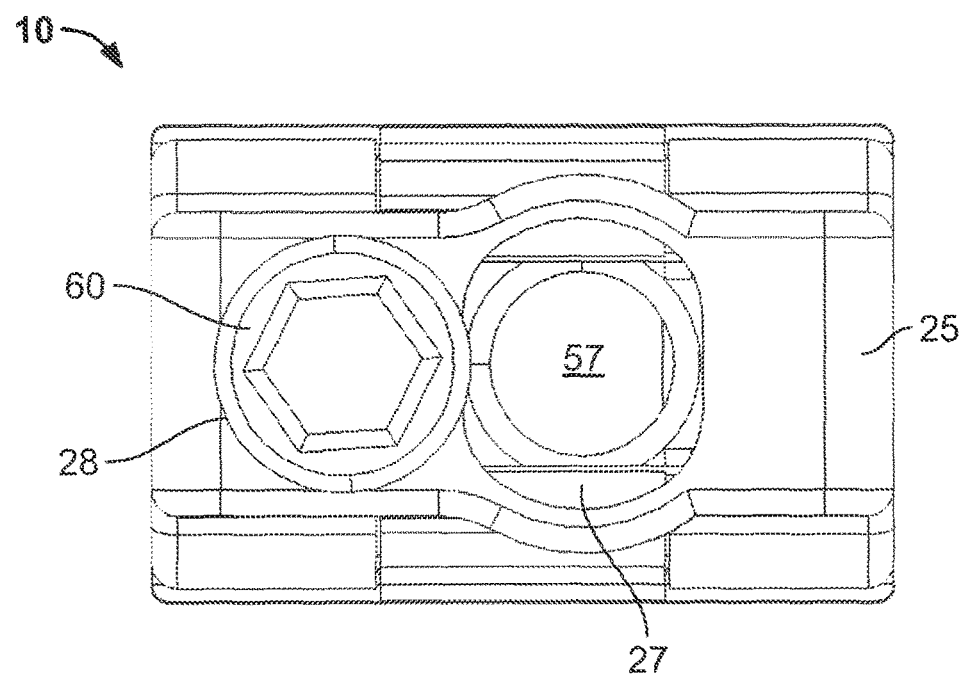
FIG. 5 is a back view of the expandable spinal fusion implant of FIG. 1.
Figure 6:
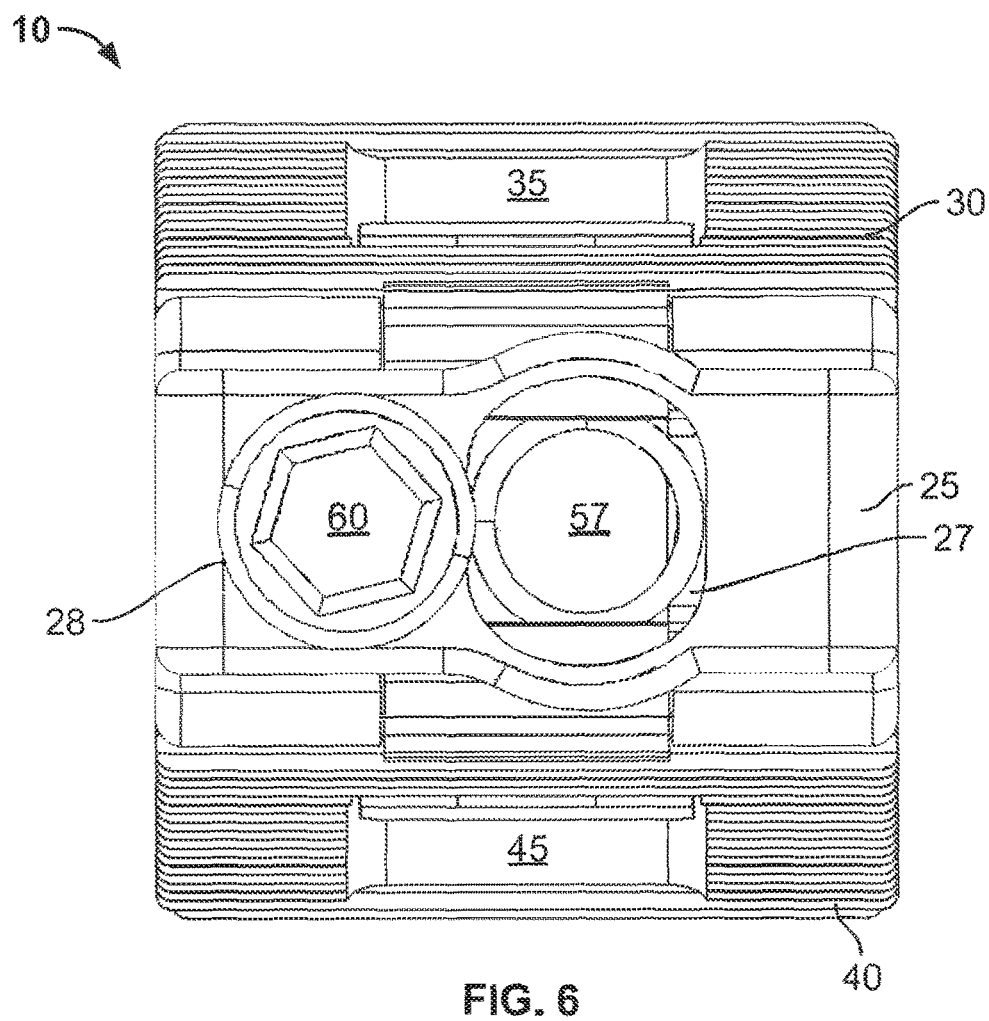
FIG. 6 is a back view of the expandable spinal fusion implant of FIG. 2.
Figure 7:
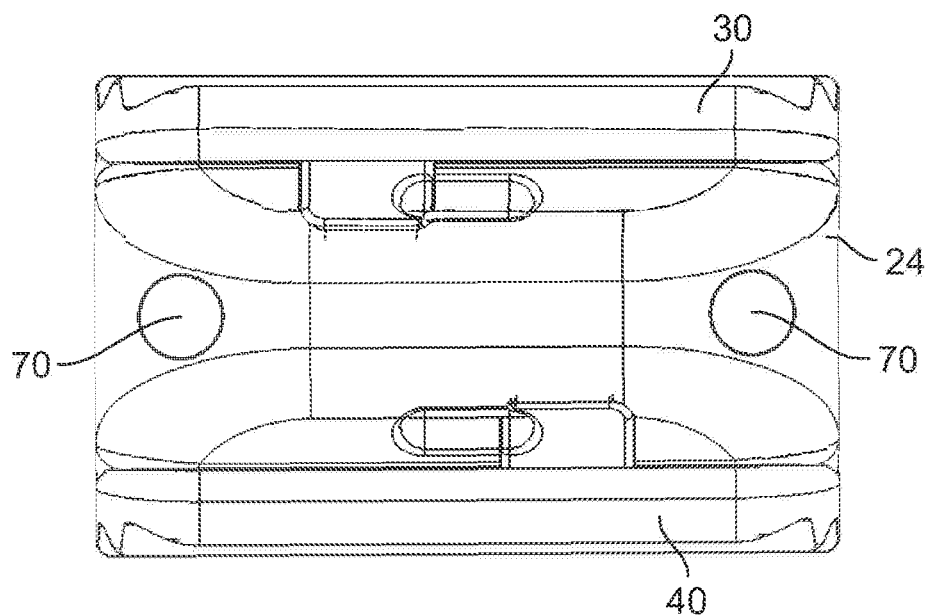
FIG. 7 is a front view of the expandable spinal fusion implant of FIG. 1.
Figure 8:
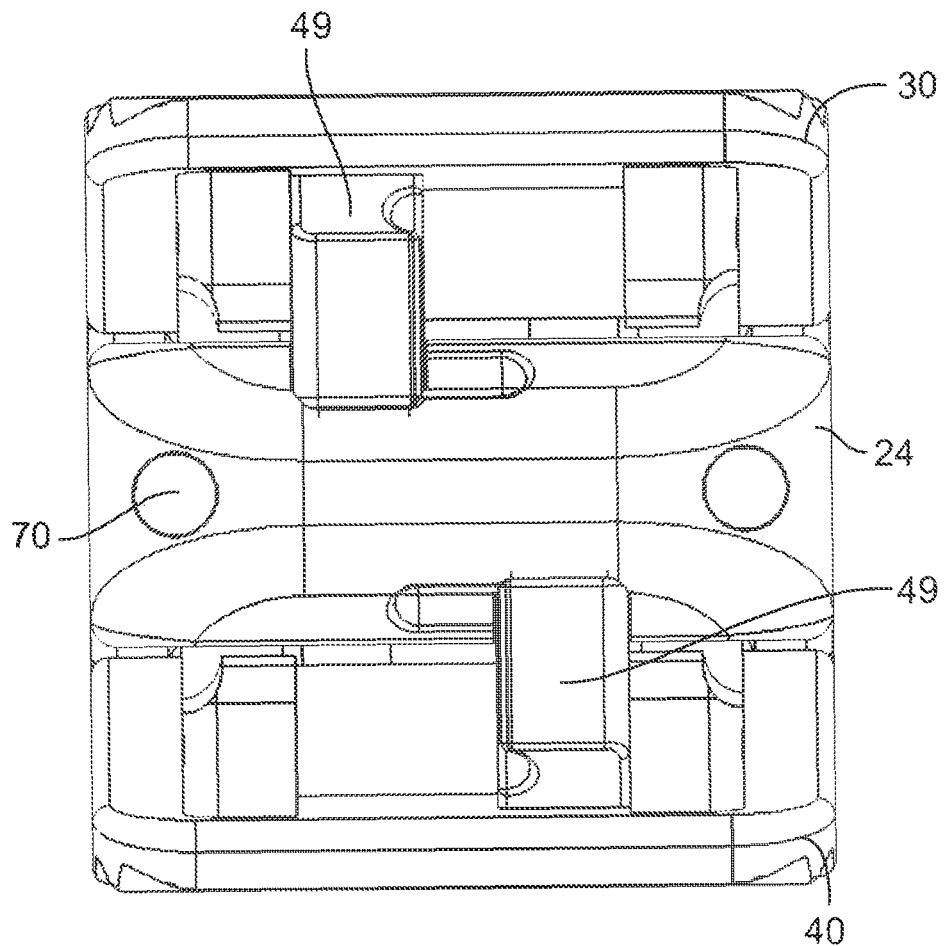
FIG. 8 is a front view of the expandable spinal fusion implant of FIG. 2.
Figure 9:
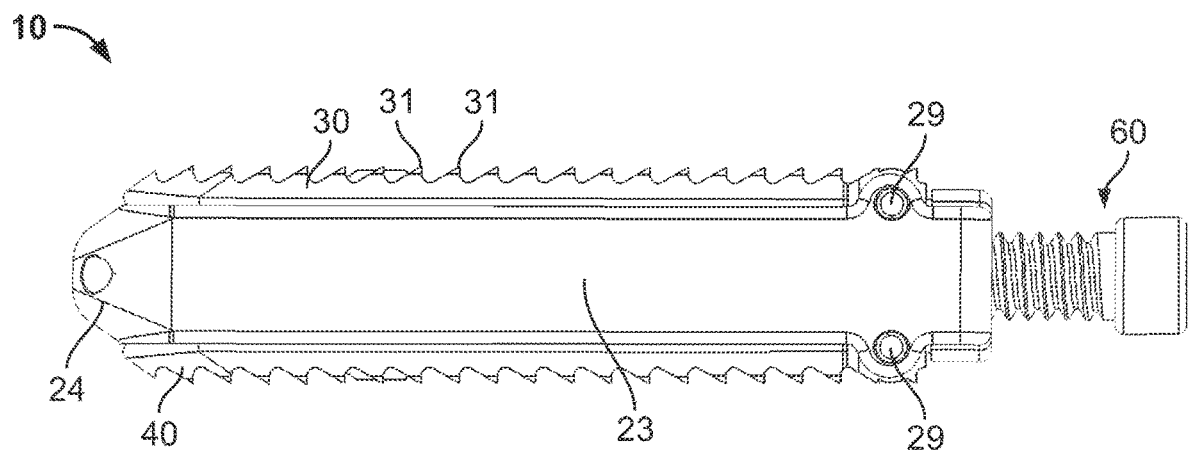
FIG. 9 is a side view of the expandable spinal fusion implant of FIG. 1.
Figure 10:
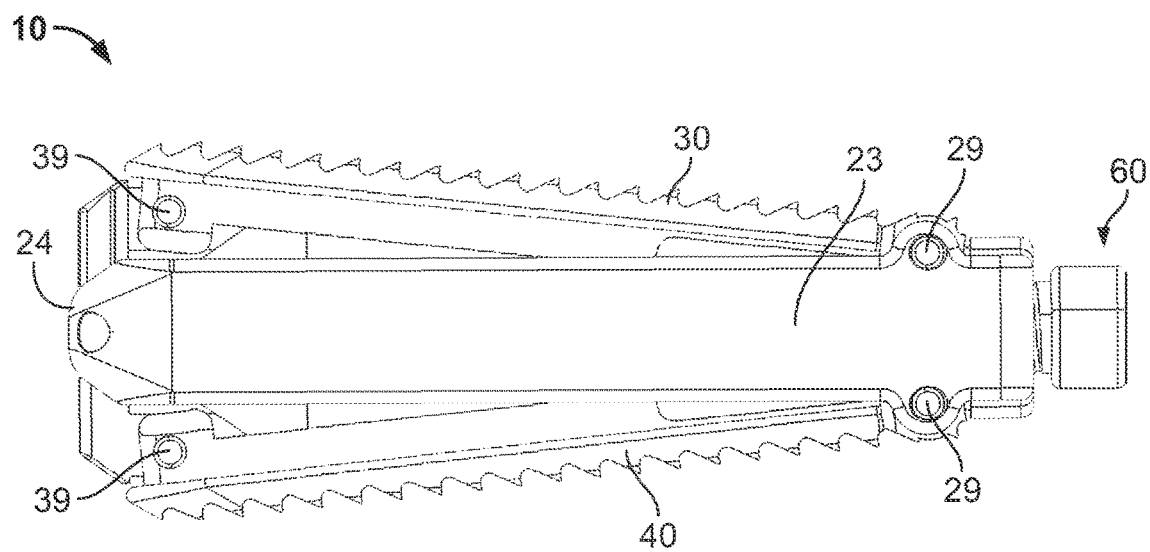
FIG. 10 is a side view of the expandable spinal fusion implant of FIG. 2.
Figure 11:
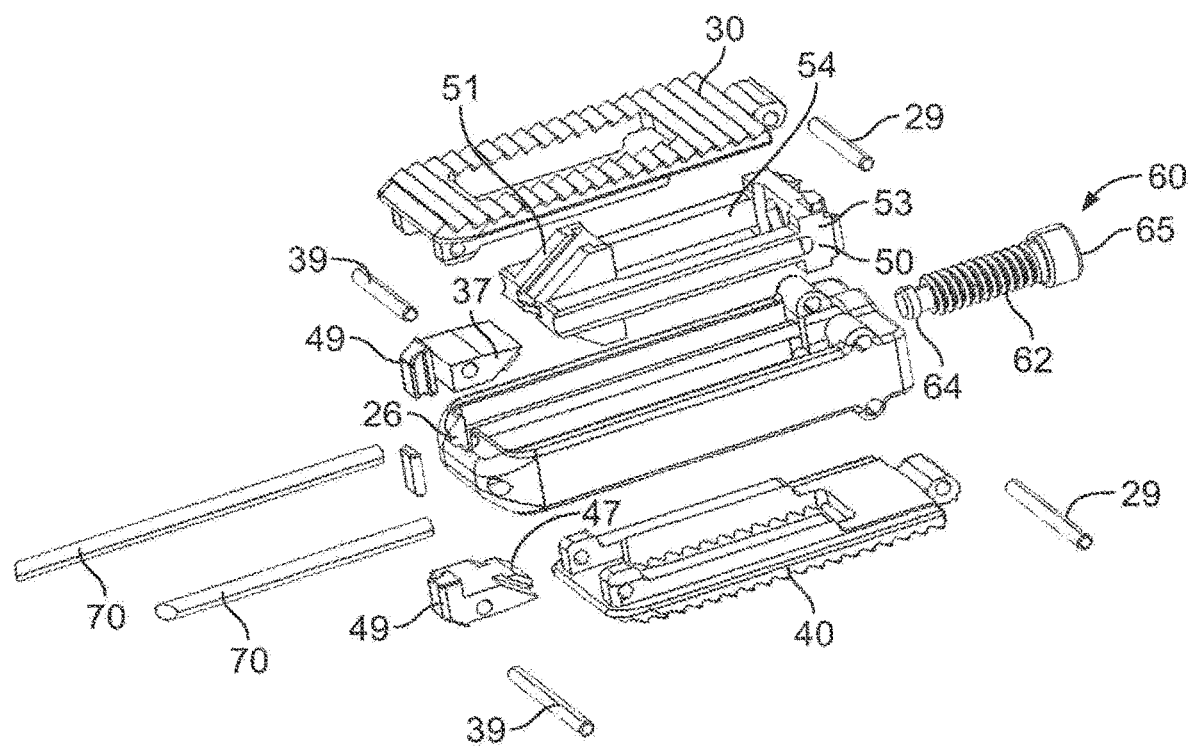
FIG. 11 is an exploded perspective view of the expandable spinal fusion implant of FIG. 1.

FIGS. 1-15 illustrate an exemplary embodiment of the expandable spinal fusion implant 10. The implant 10 includes a housing 20. The housing 20 is comprised of first and second lateral walls 22, 23, a distal or leading end wall 24 and a proximal or trailing end wall 25. The lateral walls 22, 23 and distal 24 and proximal 25 walls define a hollow interior of housing 20. According to this embodiment, the first and second lateral walls 22, 23 are of equal length and the length of the lateral walls 22, 23 spans the length of the implant 10. The distal wall 24 is tapered, increasing in height from the distal most point to the point where it meets the lateral walls 22, 23 to aid in insertion of the implant 10 into the disc space. As illustrated in the exemplary embodiment, the distal wall 24 may also include a slots 26 dimensioned to receive complementary projections 49 extending from the upper and lower endplates 30, 40. The slots comprise a first slot in the upper surface of the distal end 24 of the housing 20 for receiving a projection from the upper endplate 30 and a second slot in the lower surface of the distal end 24 of the housing 20 for receiving a projection 49 from the lower endplate 40. The proximal wall 25 of the housing is best illustrated in FIGS. 5 and 6. The proximal wall 25 includes two apertures. The first is a graft delivery port 27 and the second is a drive screw aperture 28. The drive screw aperture 28 is offset from the mid longitudinal axis of the implant 10 to facilitate packing of graft into the hollow interior of the housing 10 through the graft delivery port 27 upon implantation of the implant 10 into the disc space. The housing 20 has a static height that remains unchanged when the implant 10 is in its collapsed configuration and in its expanded configuration. The maximum height of the housing 20 is less than the maximum height of the overall implant 10.

According to the embodiment of FIGS. 1-15, the housing 20 is coupled to the upper and lower endplates 30, 40 via pins 29 adjacent the proximal end 15 of the implant 10. The upper and lower endplates 30, 40 have identical features as described below. Each endplate 30, 40 has a bone contacting surface 32, 42 and an interior surface 34, 44. The endplates 30, 40 have a width that is equal to the width of the overall implant and equal to the width of the housing 20. The perimeter of the interior surfaces 34, 44 of the endplates 30, 40 rests adjacent the lateral walls 22, 23 of the housing 20 when the implant 10 is in its collapsed configuration. The upper and lower endplates 30, 40 according to this embodiment are generally rectangular and include a central fusion aperture 35, 45. The central fusion apertures 35, 45 are in communication with the hollow interior of the housing 20 and the central fusion aperture 55 of the wedge 50 to allow for bone growth through the implant 10 after the implant 10 has been place within the disc space of a patient. The endplates further include anti-migration features 31, 41 on their respective bone contacting surfaces 32, 42. The interior surface 34, 44 of each endplate 30, 40 includes an extension 36, 46 coupled to the endplate 30, 40 via a pin 39. The extensions 36, 46 include a projection 39 at the distal end and a ramp 37, 47 at the proximal end. The ramps 37, 47 engage the superior and inferior angled surfaces 51, 52 on the wedge 50 to allow for expansion of the height of the implant 10 as the wedge 50 is driven distally within the implant 10. As illustrated in the exemplary embodiment of FIGS. 1-15, the ramps 37, 47 and angled surfaces 51, 52 of the wedge may include mating features to couple the wedge 50 to the endplates 30, 40. In the exemplary embodiment, this mating feature is a dovetail connection, though other mating features may be employed in the alternative.

As illustrated by the exemplary embodiment of FIGS. 1-15, the implant 10 includes a wedge 50 housed between the upper and lower endplates 30, 40 and within the hollow interior of the housing 20. The wedge 50 includes first and second opposing angled surfaces 51, 52 at its distal end and a drive block 53 at its proximal end. The opposing angled surfaces 51, 52 and drive block 53 are connected via a pair of lateral arms 54 extending therebetween. The opposing angled surfaces 51, 52, lateral arms 54 and drive block 53 reside inside the hollow interior of the housing 20 and define a central aperture 55 that is in communication with the central apertures 35, 45 of the upper and lower endplates 30, 40. Optionally, the lateral arms 54 of the wedge 50 may engage rails 70 that rest in between a recess in the exterior surface of the lateral arms 54 and the interior surface of the lateral walls 22, 23 of the housing 20. The drive block 53 includes a graft aperture 57 extending through its thickness. The graft aperture 57 of the drive block 53 is in communication with the graft delivery port 27 in the proximal wall 25 of the housing 20 to allow graft material to be pass through the housing 20 and wedge 50 into the interior of the implant 10. The drive block 53 also includes a receptacle 56 dimensioned to house the distal end 64 of the drive mechanism 60.

According to the exemplary embodiment of FIGS. 1-15, the drive mechanism 60 is a screw. The drive screw 60 has a proximal end 64 and a distal end 65 and a threaded shaft 62 extending between the proximal end 64 and the distal end 65. The proximal end 64 includes a mating feature 63 for engaging a driving tool (not shown). The distal end 65 is configured to complement the shape of the receptacle 56 of the drive block 53. The threaded shaft of 62 of the drive screw is configured to be received in a complementary threaded drive screw aperture 28 in the housing 20, such that as the drive screw 60 is rotated, it translates distally through the drive screw aperture 28 and consequently pushes the wedge 50 distally. When the wedge 50 is urged distally, the opposing angled surfaces 51, 52 engage the ramps 37, 47 on the endplates 30, 40 thereby increasing the distance between the distal ends of the endplates 30, 40 and increasing the distal height of the implant 10.

Figure 12:
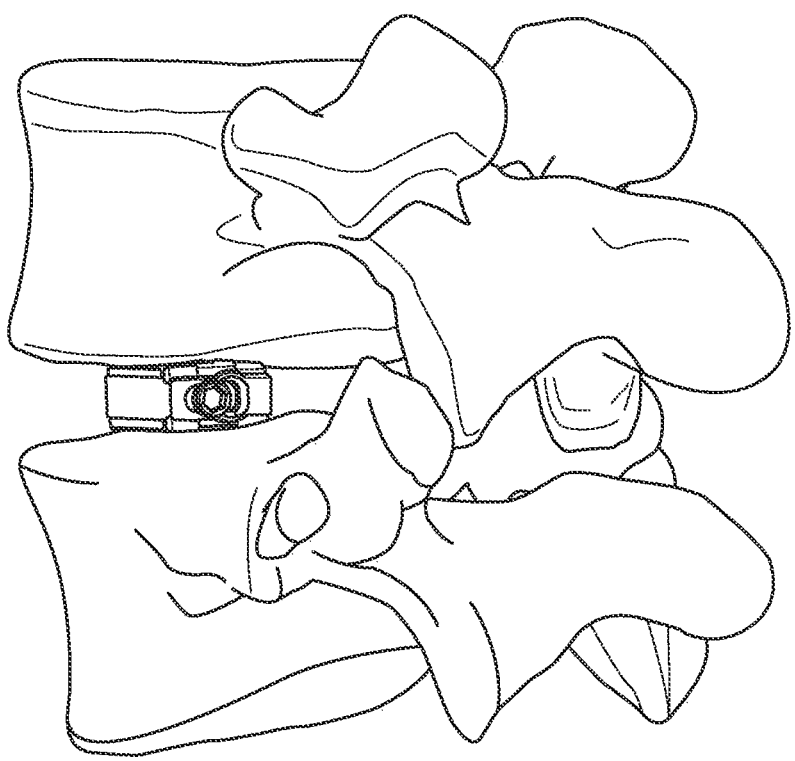
FIG. 12 is a perspective view of the expandable spinal fusion implant of FIG. 1 implanted into the intervertebral space of a spine.
Figure 13:
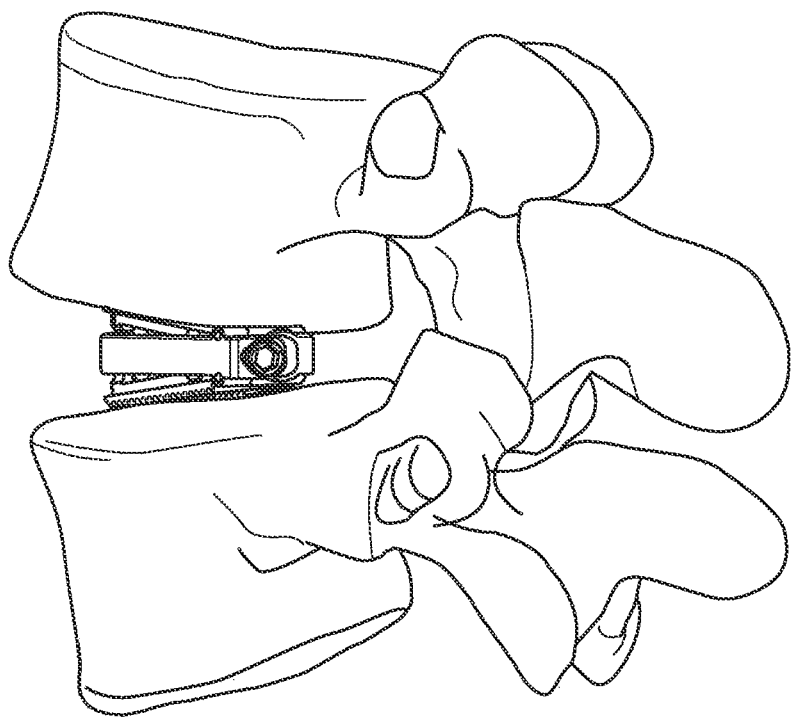
FIG. 13 is a perspective view of the expandable spinal fusion implant of FIG. 12 in its expanded configuration.
Figure 14:
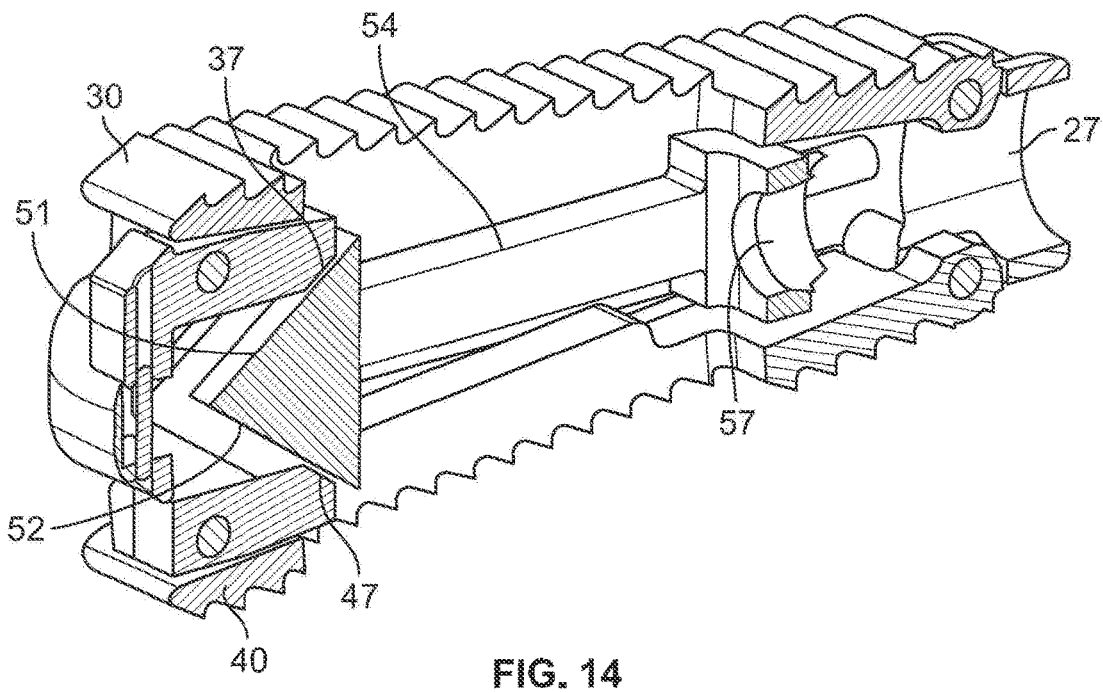
FIG. 14 is a perspective cross-sectional view of the expandable spinal fusion implant of FIG. 2.
Figure 15:
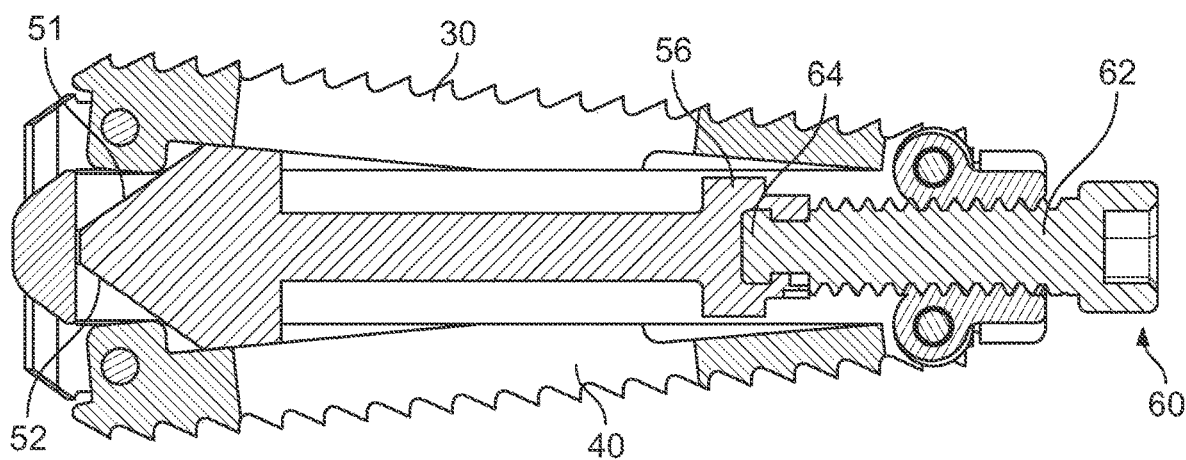
FIG. 15 is a side cross-sectional view of the expandable spinal fusion implant of FIG. 2.
Figure 16:
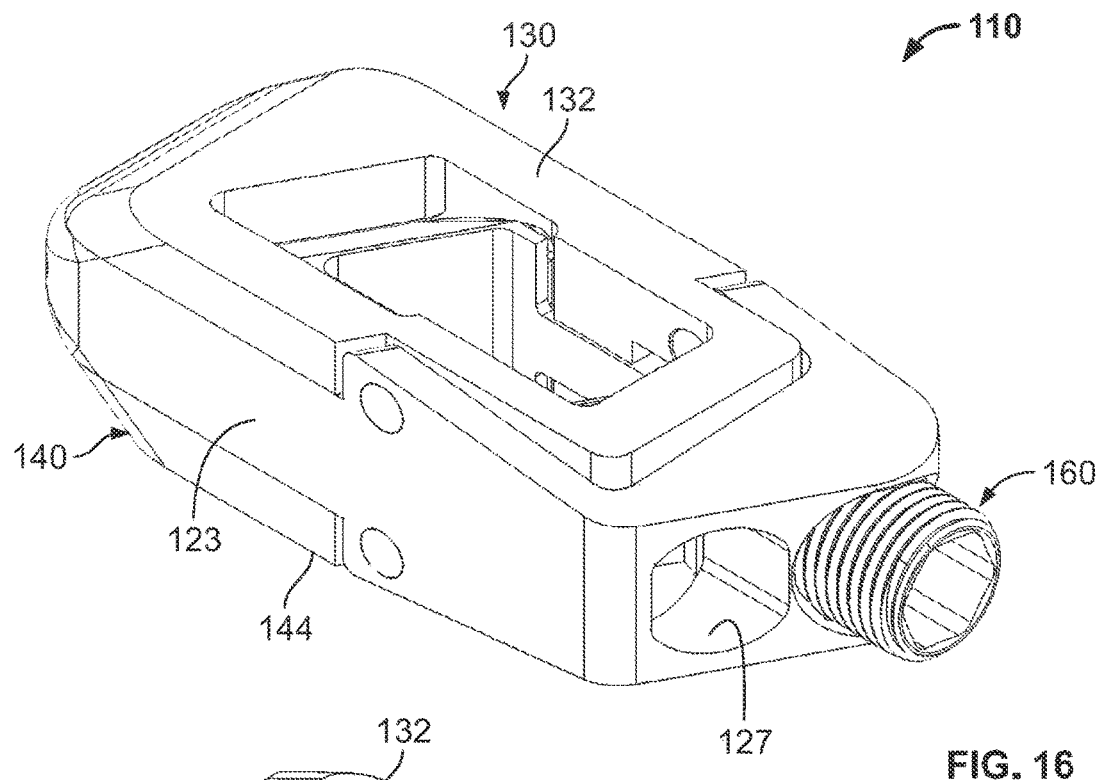
FIG. 16 is a perspective view of an expandable spinal fusion implant in a collapsed position according to an alternative embodiment.
Figure 17:
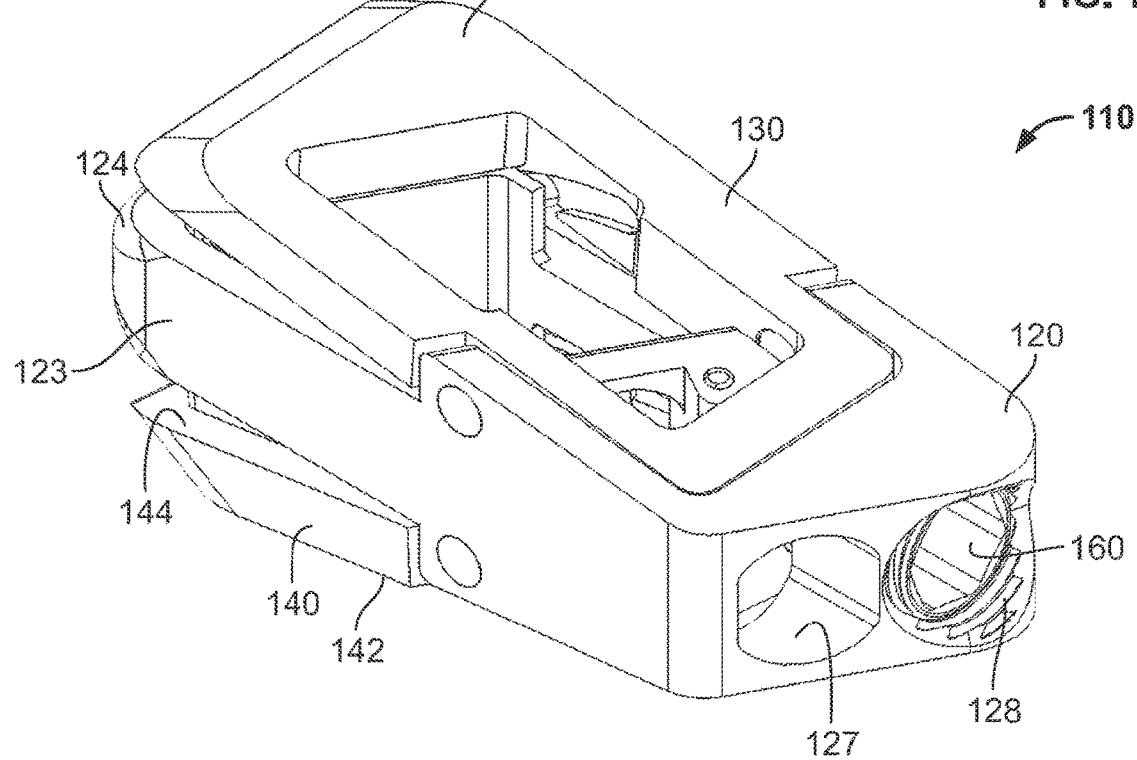
FIG. 17 is a perspective view of an expandable spinal fusion implant in an expanded configuration according to the alternative embodiment of FIG. 16.
Figure 18:
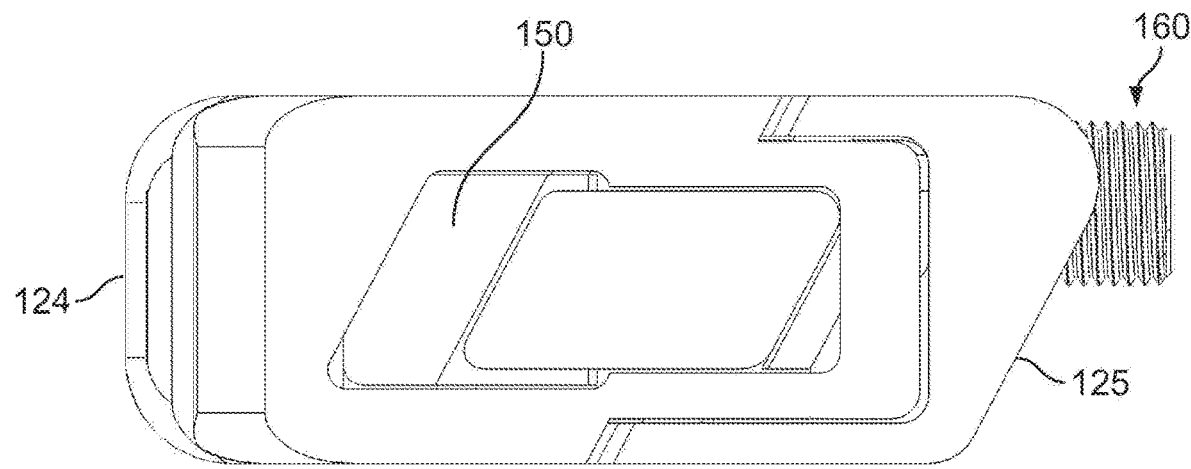
FIG. 18 is a top view of the expandable spinal fusion implant of FIG. 16.
Figure 19:
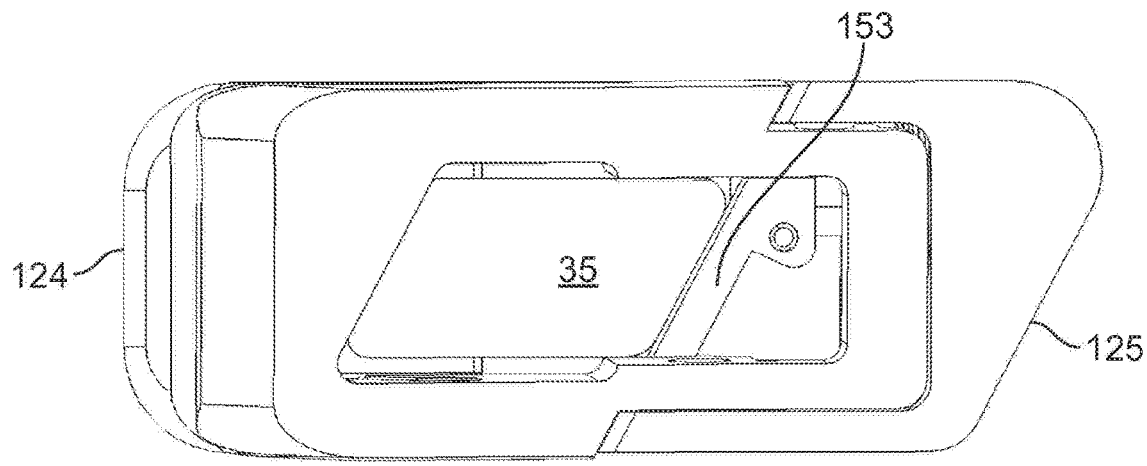
FIG. 19 is a top view of the expandable spinal fusion implant of FIG. 17.
Figure 20:
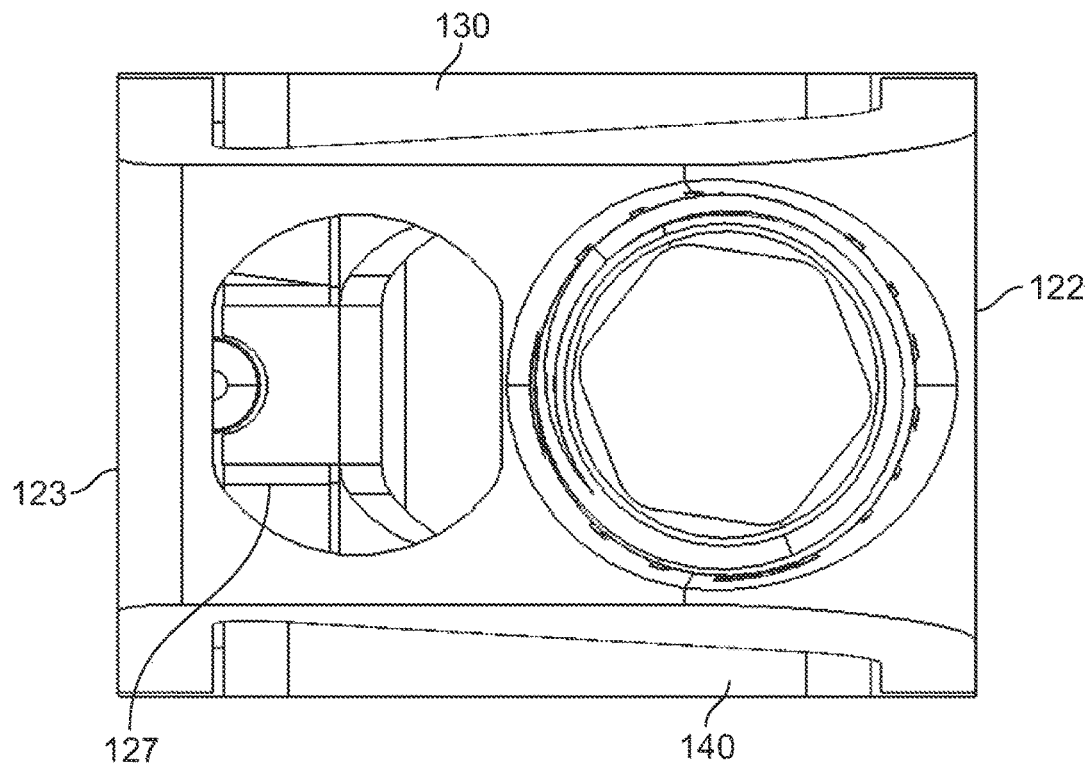
FIG. 20 is a back view of the expandable spinal fusion implant of FIG. 16.
Figure 21:
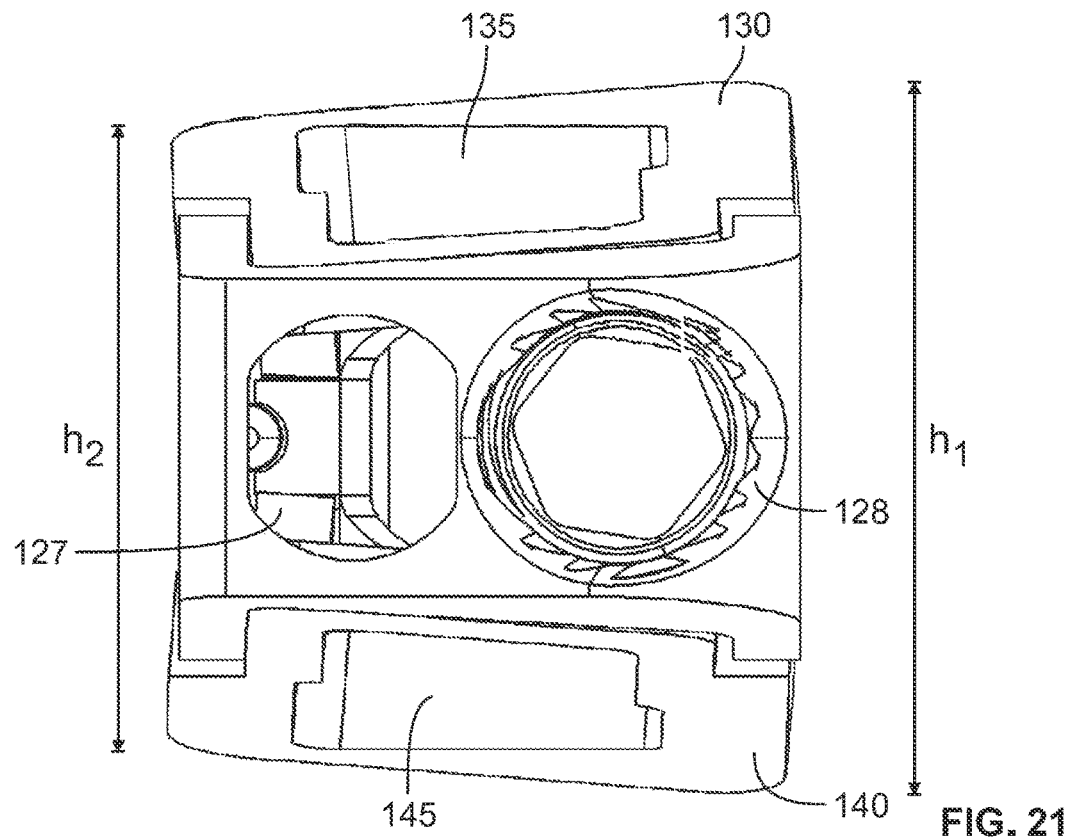
FIG. 21 is a back view of the expandable spinal fusion implant of FIG. 17.
Figure 22:
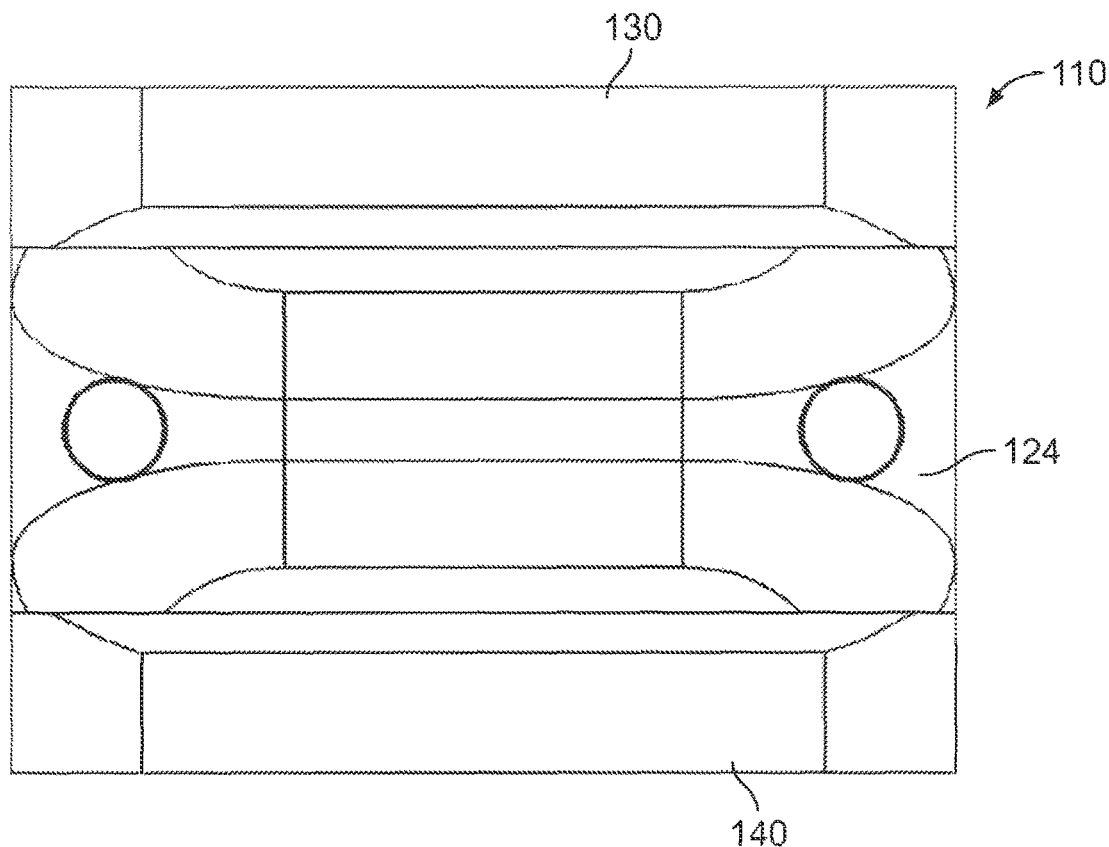
FIG. 22 is a front view of the expandable spinal fusion implant of FIG. 16.

In use according to this exemplary embodiment, the implant 10 implant is inserted into the disc space between adjacent vertebral bodies in its collapsed position as illustrated in FIG. 12. The collapsed configuration of the implant is illustrated in FIGS. 1, 3, 5, 7 and 9. Once the implant 10 has been placed in the desired position within the disc space, the drive screw 60 is engaged with a driving tool and rotated to advance the drive screw 60 distally within the implant, thereby advancing the wedge 50 distally and causing the upper and lower endplates 30, 40 to separate at the distal end 14 of the implant 10. When the drive screw has been fully advanced, the implant 10 is in its fully expanded configuration as illustrated in FIG. 13. Upon desired expansion of the implant, graft material is inserted into the interior of the implant through the graft delivery port 27 and graft aperture 57 of the wedge in the proximal end of the implant.

FIGS. 16-27 illustrate an alternative embodiment of the expandable spinal fusion implant 110. The implant 110 according to this alternative embodiment has many of the same features as described for the implant 10 in FIGS. 1-15 which are not necessarily repeated in detail here. The implant 110 according to the alternative embodiment shown in FIGS. 16-27 is an oblique implant, meaning it is dimensioned to be inserted into the disc space at an angle that is oblique to the midline of the disc space. For example, this implant insertion trajectory is common in a transforaminal lumbar interbody fusion (TLIF) surgical procedure. The implant 110 according to the alternative embodiment is similar in structure to the one described in FIGS. 1-15 in that it includes a housing 120, upper and lower endplates 130, 140, a wedge 150 and a drive mechanism 160 which are described in further detail below.

According to the embodiment of FIGS. 16-27, the implant 110 has a housing 120. The housing has the same structure as previously described, including a distal wall 124, a proximal wall 125 and first and second lateral walls 122, 123 extending between the distal and proximal walls 124, 125. The four walls define a hollow interior of the housing 120. However, the housing 120 according to the alternative embodiment is different in that the first lateral wall 122, the anterolateral wall when the implant 120 is positioned in the disc space, is greater in length than the second lateral wall 123 (the posterolateral wall). The distal wall 124 is tapered to aid in insertion of the implant 110 into the disc space. The proximal wall 125 includes a threaded drive screw aperture 127 and a graft delivery port 128. The drive screw aperture 127 is offset from the midline of the implant 110 and configured to receive the drive mechanism 160 therethrough. The height of the housing 120 is static, remaining unchanged when the implant 110 is in its collapsed configuration and its expanded configuration. The maximum height of the housing 120 is less than the maximum height of the overall implant 110.

Figure 23:
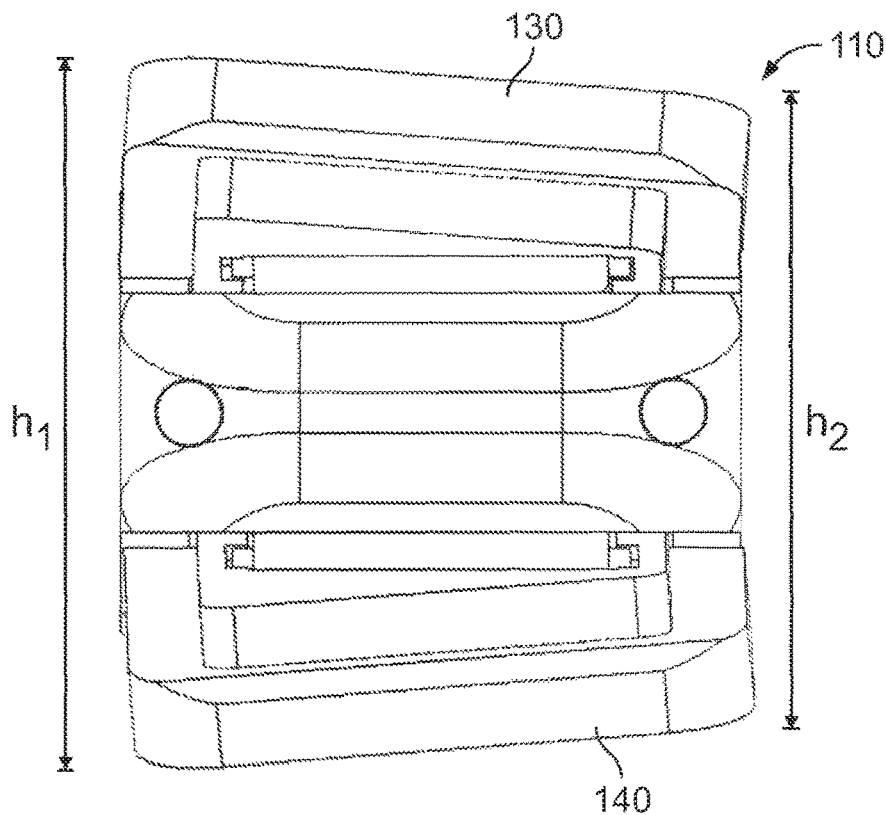
FIG. 23 is a front view of the expandable spinal fusion implant of FIG. 17.
Figure 24:
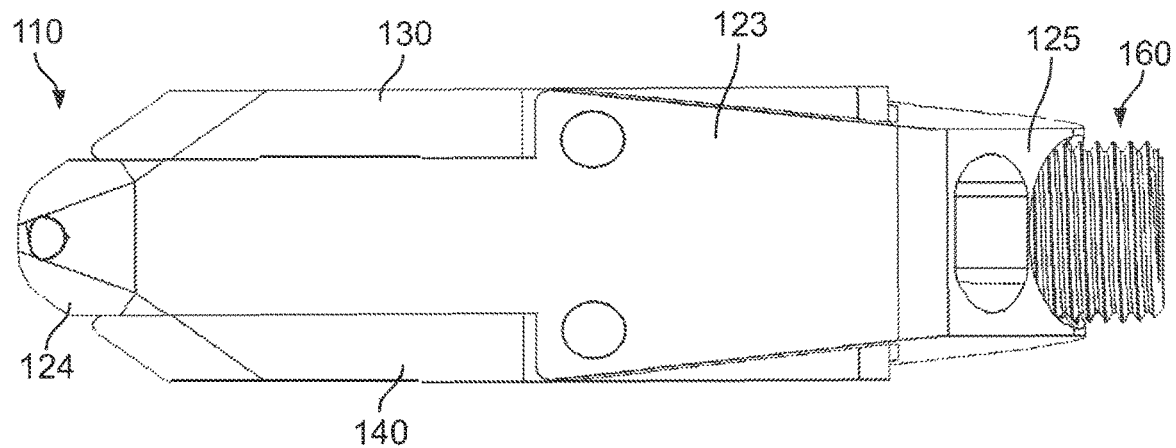
FIG. 24 is a first side view of the expandable spinal fusion implant of FIG. 16.
Figure 25:
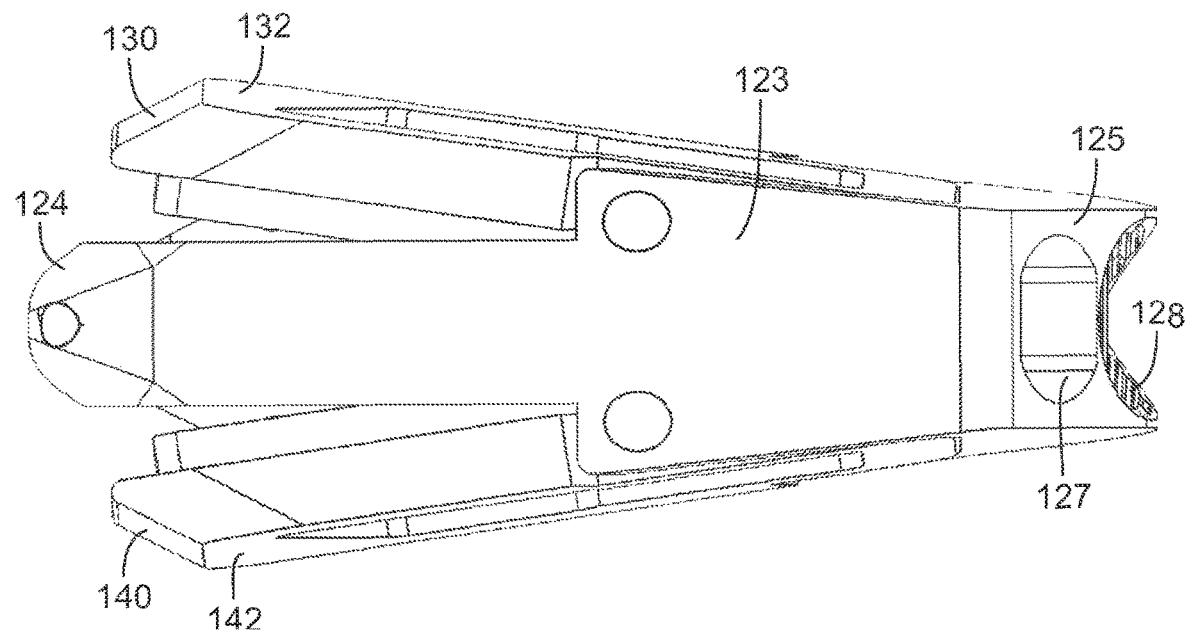
FIG. 25 is a first side view of the expandable spinal fusion implant of FIG. 17.
Figure 26:
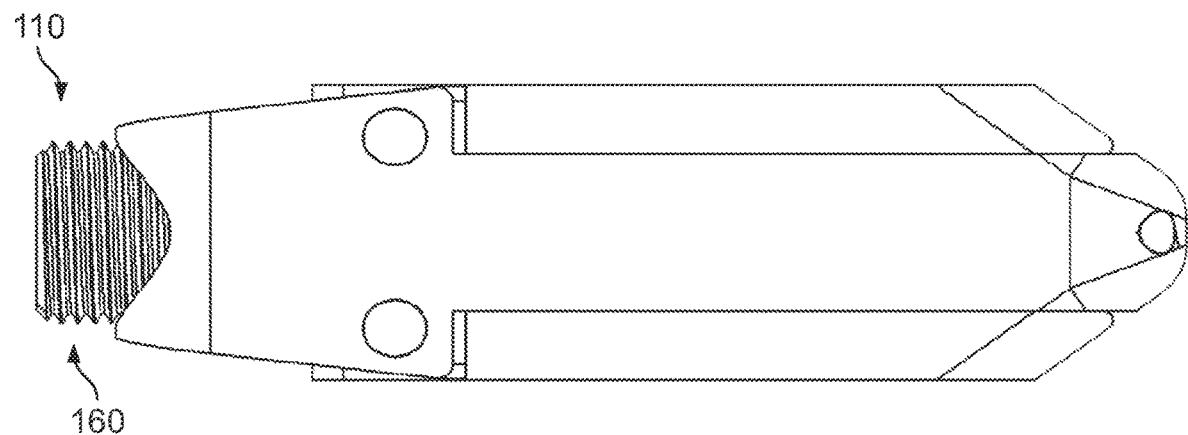
FIG. 26 is a second side view of the expandable spinal fusion implant of FIG. 16.
Figure 27:
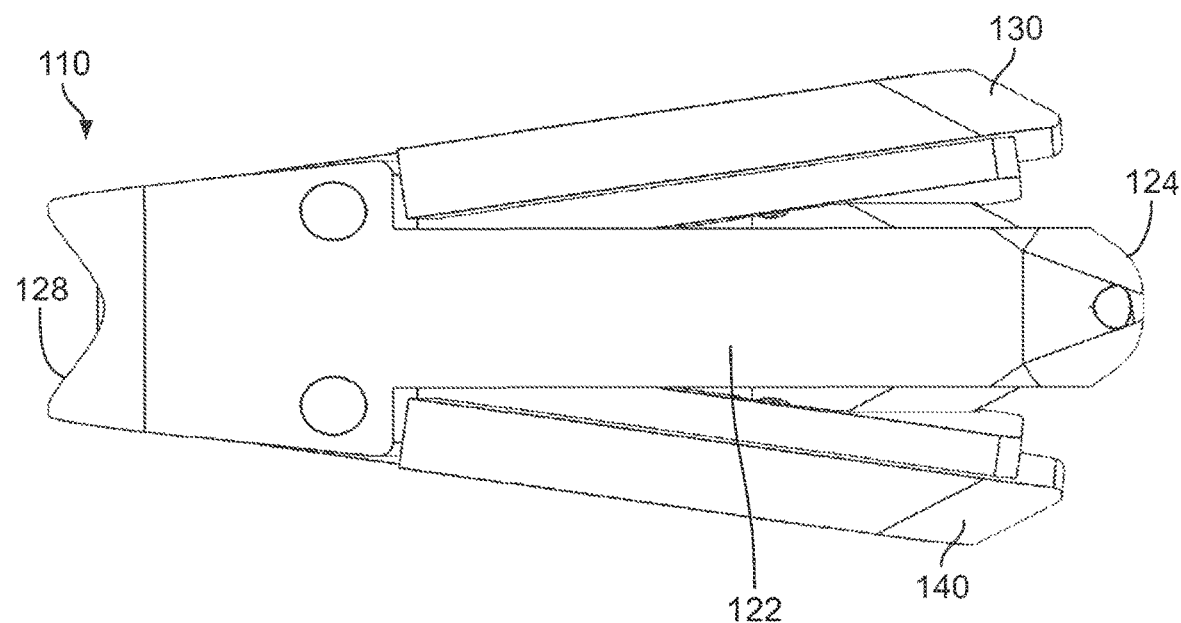
FIG. 27 is a second side view of the expandable spinal fusion implant of FIG. 17.
Figure 28:
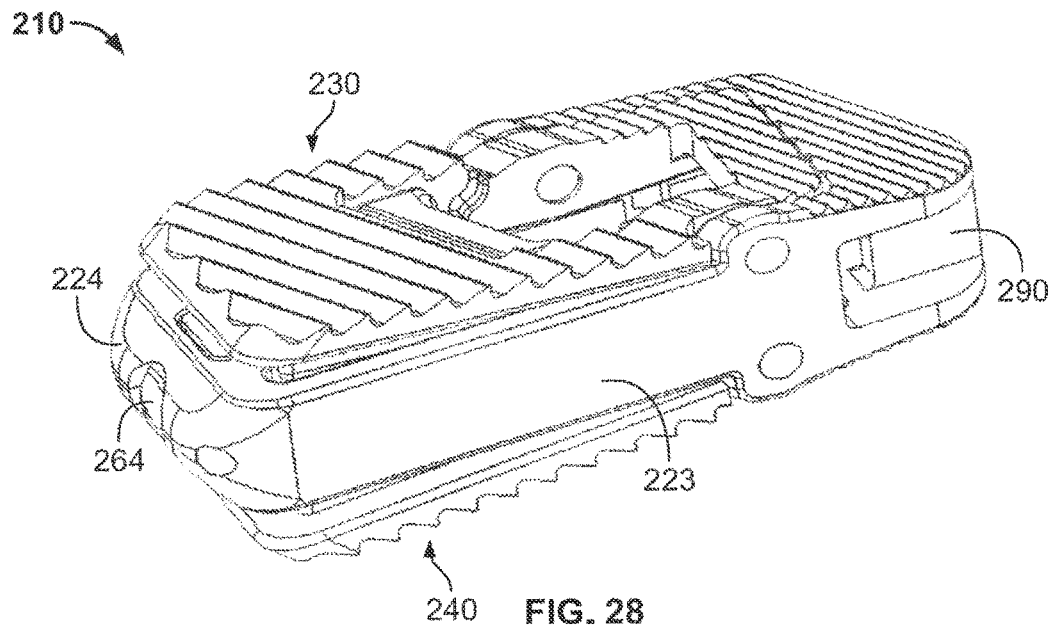
FIG. 28 is a perspective view of an expandable spinal fusion implant according to another alternative embodiment.
Figure 29:
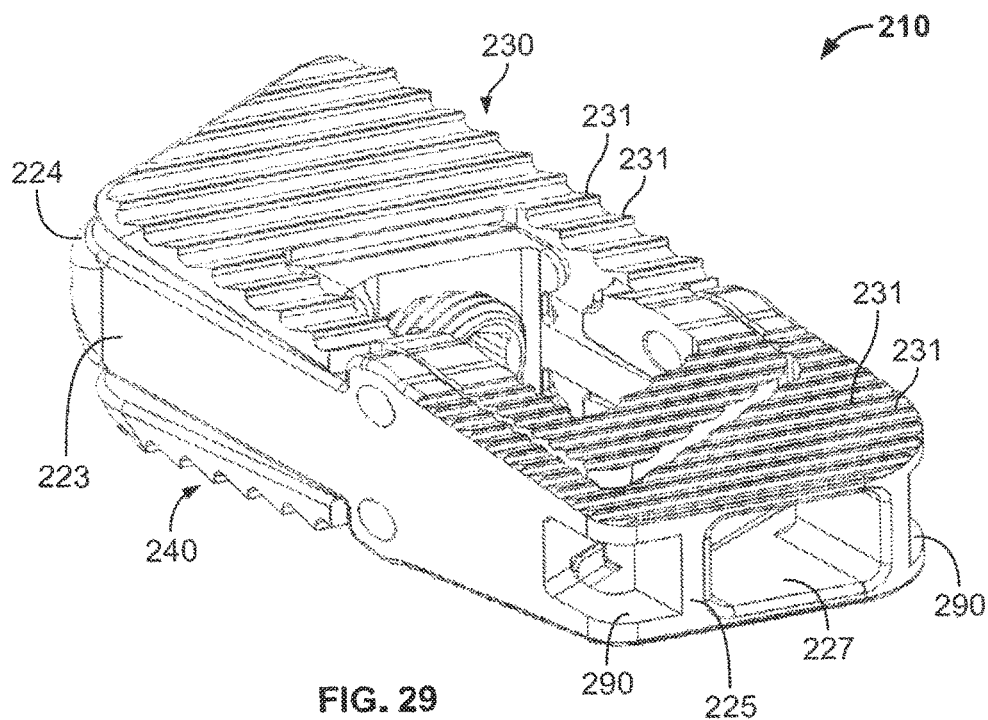
FIG. 29 is a rear perspective view of the expandable spinal fusion implant of FIG. 28.
Figure 30:
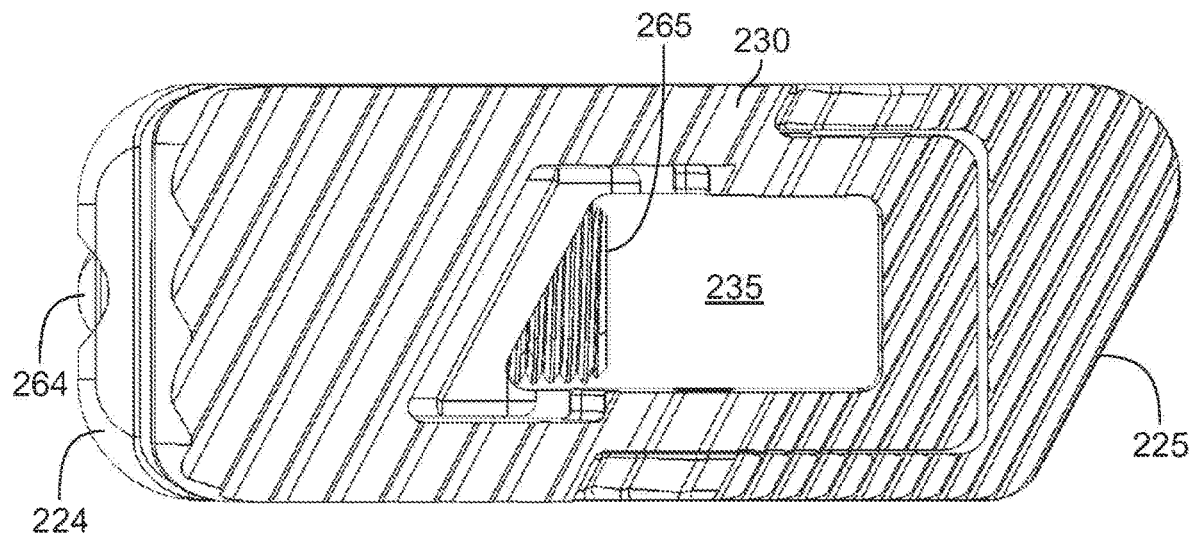
FIG. 30 is a top view of the expandable spinal fusion implant of FIG. 28.
Figure 31:
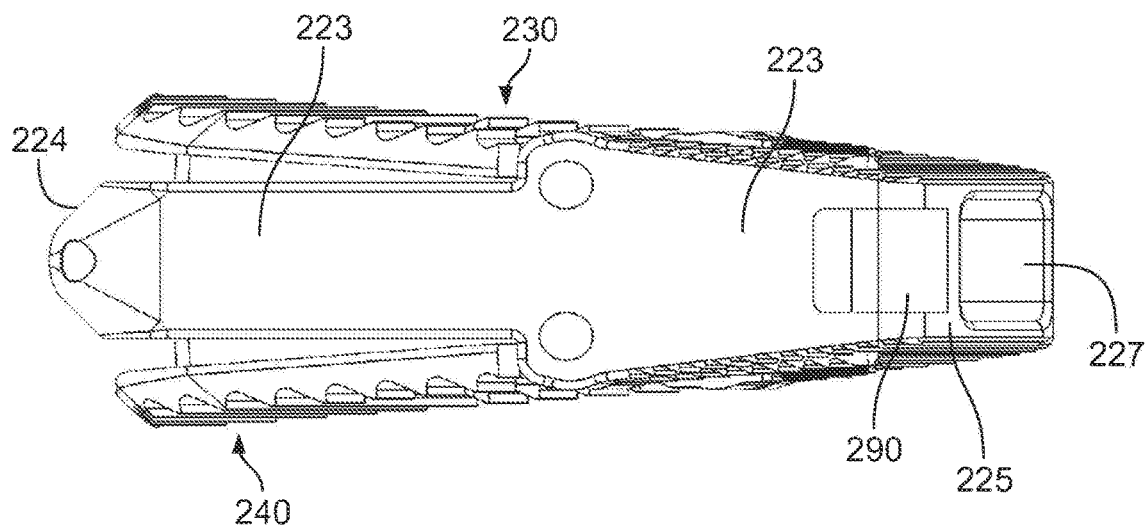
FIG. 31 is a first side view of the expandable spinal fusion implant of FIG. 28.
Figure 32:
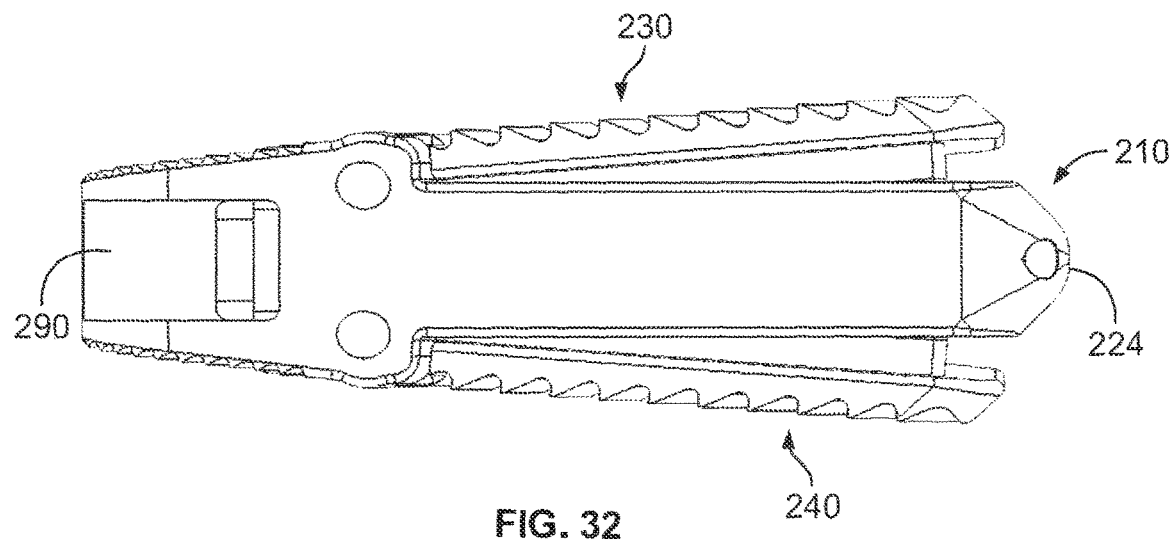
FIG. 32 is a second side view of the expandable spinal fusion implant of FIG. 28.

The upper and lower endplates 130, 140 according to this alternative embodiment are identical, mirror images of each other. The endplates 130, 140 of the alternative embodiment differ from the endplates 30, 40 of the previously described embodiment in that they increase in height across the endplate 130, 140 from the proximal end 133, 143 to the distal end 131, 141 of the endplate 130, 140 and from the posterolateral side 136, 146 to the anterolateral side 138, 148 of the endplate 130, 140. As a result, when the implant 120 is in its fully expanded configuration, the anterolateral height $h_1$ of the implant 110 is greater than the posterolateral height $h_2$ of the implant, as best shown in FIGS. 23 and 25. Each endplate 130, 140 further comprises a bone contacting surface 132, 142 and an interior surface 134, 144. Although not illustrated in FIGS. 16-27, it is contemplated that the bone contacting surfaces 132, 142 could include antimigration features. The interior surfaces 134, 144 of the endplates 130, 140 include a ramped surface 137, 147 at the distal end of the endplate 131, 141 that engage opposing angled surfaces 151, 152 on the wedge 150. According to the embodiment shown in FIGS. 16-27, the interior side surfaces of the endplates include slots 139, 149 for receiving projections 126 on the sides of the wedge 150.

According to the alternative embodiment, the wedge 150 is similar in structure to the wedge 50 as previously described. The wedge 150 has opposing angled surfaces 151, 152 at its distal end and a drive block 153 at its proximal end. The opposing angled surfaces 151, 152 and drive block 153 are coupled via a pair of lateral arms 154 defining a central aperture 155 therebetween. The drive block 153 similarly includes a graft aperture 157 through its thickness and a drive screw receptacle 158 dimensioned to house the distal end 164 of the drive screw 160.

The drive mechanism 160 of this alternative embodiment is similar in form and in function to the drive screw mechanism 60 described for the previous embodiment. The drive mechanism 160 is a drive screw. The drive screw 160 has a distal end 164 dimensioned to be received within the receptacle 158 of the drive block 153 and a proximal end 165 equipped with a mating feature for engaging a drive tool (not shown) and a threaded shaft 162 extending between the proximal end and distal end. As the drive screw 162 is rotated, the threads on the shaft 162 engage the complementary threads on the drive screw aperture 128 of the housing 120 allowing the drive screw to translate distally into the implant 110 thereby urging the wedge 150 distally within the implant and causing the endplates 130, 140 to separate.

FIGS. 28-36 illustrate yet another alternative embodiment of an expandable spinal fusion implant 210 in a partially expanded state. As with the embodiment illustrated in FIGS. 16-27, the current embodiment is designed to be an oblique implant for use in a TLIF procedure. The embodiment illustrated in FIGS. 28-36 includes the same basic structures as the two previous embodiments, including a housing 220, upper and lower endplates 230, 240, a wedge 250 and a drive mechanism 260. These structures are described in further detail in the following paragraphs.

According to the third embodiment of FIGS. 28-36, the implant 210 includes a housing 220. The housing 220 has a distal wall 224, a proximal wall 225 and first and second lateral walls 222, 223 defining a hollow interior. The distal wall 224 of the housing 220 is tapered from where it meets the lateral walls 222, 223 to the distal most point of the distal wall to aid in insertion of the implant 210 into the disc space. The distal wall 224 includes a drive mechanism aperture 228 configured to receive the distal end of the drive mechanism 260. The proximal wall 225 has first and second bone contacting surfaces 229 and a graft delivery port 227 extending through its thickness. The proximal wall 225 may also include channels 290 for receiving arms of an insertion tool (not shown) As illustrated in FIGS. 28-36, it is contemplated that the bone contacting surfaces 229 of the proximal wall 225 include anti-migration features 231, 241. The height of the housing 220 is static, remaining unchanged when the implant 210 is in its collapsed configuration and in its expanded configuration. The first lateral wall 222, the anterolateral wall of the implant when the implant is positioned within the disc space, has a length that is greater than the length of the second lateral wall 223 (the posterolateral wall). It is contemplated that the housing 220 can be manufactured of metal or PEEK.

Figure 33:
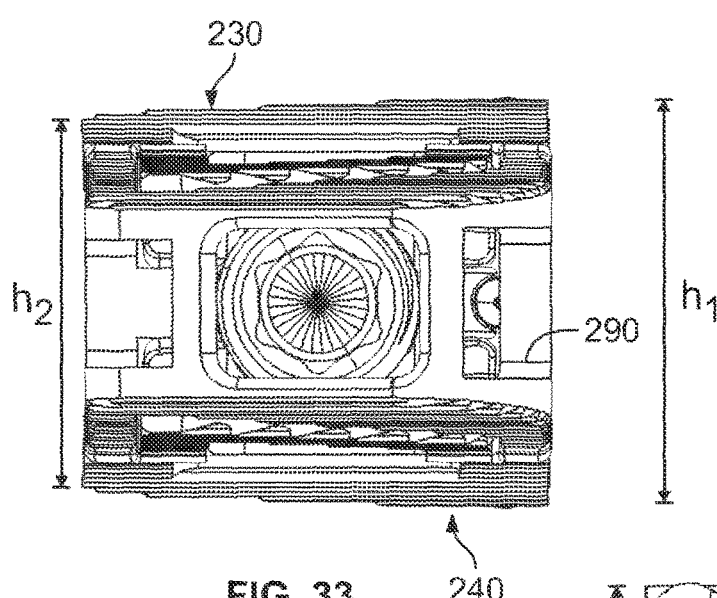
FIG. 33 is a back view of the expandable spinal fusion implant of FIG. 28.
Figure 34:
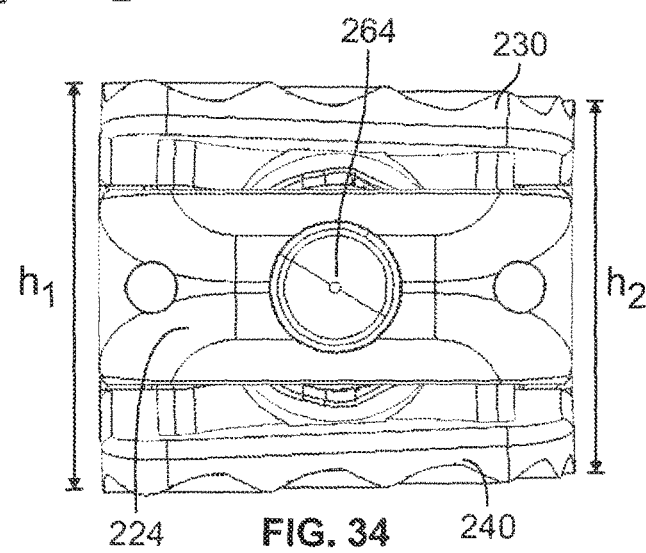
FIG. 34 is a front view of the expandable spinal fusion implant of FIG. 28.
Figure 35:
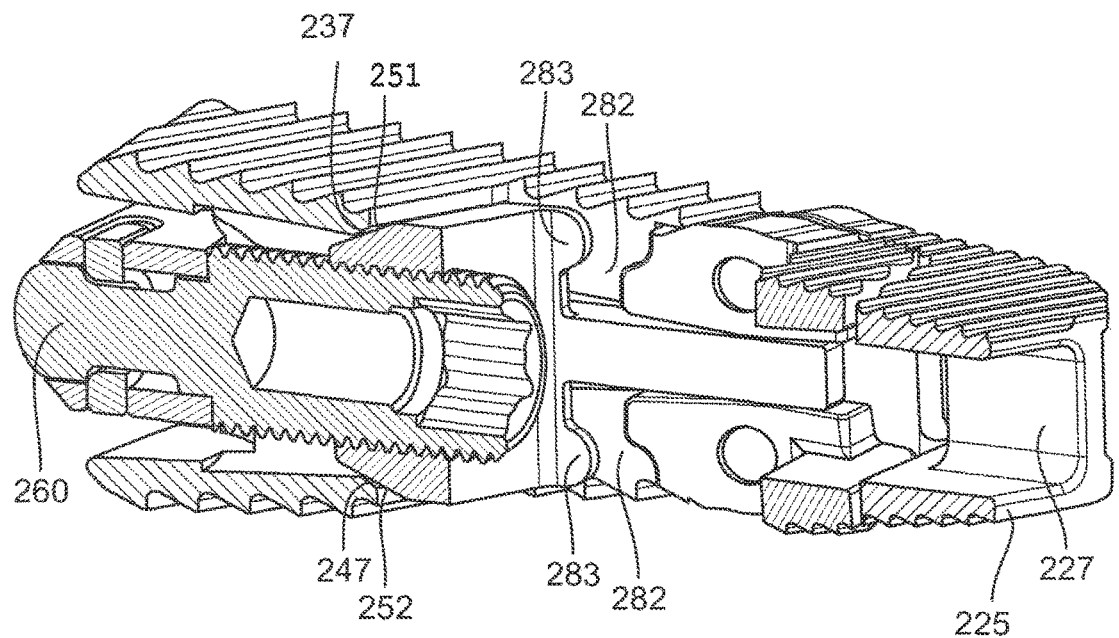
FIG. 35 is a perspective cross-sectional view of the expandable spinal fusion implant of FIG. 28.
Figure 36:
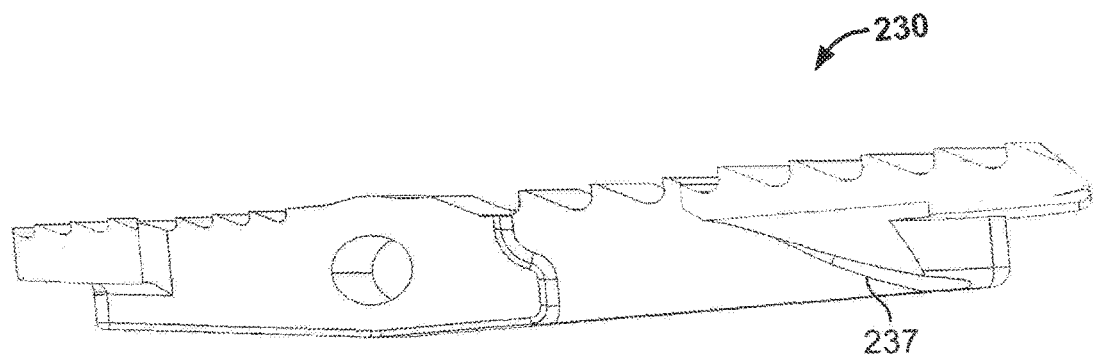
FIG. 36 is a side cross-sectional view of the upper endplate of the expandable spinal fusion implant of FIG. 28.

According to the embodiment shown in FIGS. 28-36, the housing is coupled to the upper and lower endplates 230, 240 via pins 239. The upper and lower endplates 230, 240 are identical, mirror images of each other. Each endplate 230, 240 has a bone contacting surface 232, 242 and an interior surface 234, 244. The bone contacting surfaces 232, 242 may include anti-migration features 239. The endplates 230, 240 include a central fusion aperture 235, 245 in communication with the hollow interior of the housing 220 to allow bone growth through the implant 210 after the implant has been placed within the disc space of patient. Each endplate 230, 240 further includes an interior side walls 272, 273 having a recess 282 and a projection 283 for engaging proximal projections 259 on the wedge 260. When the projections 283 on the interior side walls 272, 273 of the endplates are engaged with the proximal projections 259 on the wedge 250, the upper and lower endplates 230, 240 are locked in the collapsed configuration until such time as the wedge 260 is translated distally and the projections 283, 259 are disengaged. The interior surfaces 234, 244 of the endplates 230, 240 include a ramp 237, 247 adjacent the distal end of the endplates 230,240 that engage the opposing angled surfaces 251,252 on the wedge 250 to facilitate the expansion of the distal end 214 of the implant 210. As best illustrated in FIG. 36, the ramp 237, 247 is slightly radiused. While illustrated here as having a radiused ramp 237 and a generally planar angled surface 251, 252 on the wedge, it is contemplated that the ramp 237, 247 could be planar and the opposing angled surfaces 251, 252 on the wedge could be radiused. Alternatively, it is contemplated that both the ramp 237, 247 and the opposing angled surfaces 251, 252 could be planar or both could be radiused. As best seen in FIGS. 33 and 34, the endplates 230, 240 have a greater height on the anterolateral sides 232, 242 of the distal ends 234, 244 of the end plates such that when the implant is in its fully expanded state, the overall height of the implant is both greater at the distal end of the implant than at the proximal end of the implant but also the height $h_1$ on the anterolateral side of the implant is greater than the height $h_2$ on the posterolateral side of the implant.

The wedge 250 according to the third embodiment is housed in the hollow interior of the housing 220 and between the interior surfaces 234, 244 of the upper and lower endplates 230, 240. The wedge 250 has a distal face defined by opposing angled surfaces 251, 252 and a proximal face 293. The wedge has a threaded drive mechanism aperture 258 extending throughout the wedge from the proximal face 243 through the distal face dimensioned to receive a threaded shaft 262 of the drive mechanism 260. As previously mentioned, the wedge has projections 259 extending from the proximal face 293 for engaging projections 283 on the interior side walls 272, 273 of the endplates 230, 240. The wedge 250 is positioned in the interior of the implant 210 such that when the implant 210 is in its collapsed configuration the wedge 250 is sitting in the hollow interior and blocking the distal portion of the central fusion apertures 235, 245 of the endplates 230, 240. When the implant 210 is in its fully expanded configuration, the wedge has been urged distally and thus is blocking less of the central fusion apertures 235, 245 effectively increasing the size of the aperture extending through the implant 210.

According to the embodiment shown in FIGS. 28-36, the drive mechanism 260 includes a threaded shaft 262 having a proximal end 265 including an engagement feature 267 for mating with a drive tool (not shown). The distal portion 264 of the drive mechanism 260 extends distally from the threaded shaft 262 and is configured to be anchored in the distal wall 224 of the housing 220. The distal portion of the drive mechanism 260 is non-threaded, and is allowed to rotate within the drive mechanism aperture 227 in the distal wall 224 of the housing without translating. As the drive mechanism 260 is rotated by a drive tool, the threaded shaft engages complementary threads inside the threaded aperture 258 extending through the wedge 250 and causes the wedge 250 to translate distally until the implant 210 is fully expanded.

In use, the expandable spinal fusion implant 210 is inserted into a disc space between adjacent vertebral bodies in its collapsed configuration. Although not shown, it is contemplated that an insertion tool having two arms extending from the distal end will engage the insertion tool channels 290 on the proximal wall 225 of the housing 220. The insertion tool has a hollow shaft to allow the drive mechanism driver to be inserted therethrough. The distal end of the drive mechanism driver is inserted through the graft delivery port 227 in the housing 220 and engaged with the mating feature 267 of the drive mechanism 267. The drive mechanism driver is used to rotate the drive mechanism thereby causing the wedge 260 to translate distally between the upper and lower endplates 230, 240. Then the driver is disengaged from the drive mechanism and withdrawn from the hollow shaft of the insertion tool. Subsequently, graft material is inserted through the hollow shaft of the insertion tool, through the graft delivery port 227 in the proximal wall 224 of the housing 220 and into the hollow interior of the implant 210. In an exemplary embodiment, a sufficient amount of graft is inserted to fill the interior of the implant, through the central apertures 235, 245 in the endplates such that there is graft in compact contact with the endplates of each of the adjacent vertebral bodies.

A number of embodiments of the invention have been described. Nevertheless, it will be understood that various modifications may be made without departing from the spirit and scope of the invention. Accordingly, other embodiments are within the scope of the following claims.

What is claimed is:

1. An expandable implant comprising:
a housing including a proximal wall and a distal wall;
a first endplate moveably attached to the housing and having a first interior surface including a first ramp, and a second endplate moveably coupled to the housing and having a second interior surface including a second ramp;
a wedge positioned at least partially within the housing, the wedge including a first surface configured to engage the first ramp and a second surface configured to engage the second ramp; and
a drive mechanism configured to engage the proximal wall of the housing and drive the wedge relative to the housing, thereby moving the expandable implant from a collapsed configuration to an expanded configuration,
wherein in the expanded configuration, a height between the first and second endplates increases along a direction from the proximal wall toward the distal wall of the housing, and wherein the distal wall of the housing is free of the drive mechanism,
wherein the first and second endplates each include: an interior side wall having a recess, and a projection configured to engage the wedge and lock the first and second endplates in the collapsed configuration.

2. The implant of claim 1, wherein a height of the housing is uniform.

3. The implant of claim 1, wherein the housing further comprises an anterolateral sidewall and a posterolateral sidewall.

4. The implant of claim 3, wherein the anterolateral sidewall has a length that is greater than a length of the posterolateral sidewall.

5. The implant of claim 3, wherein in the expanded configuration, the height between the first and second endplates increases along a direction from the posterolateral sidewall toward the anterolateral sidewall of the housing.

6. The implant of claim 1, wherein the first endplate comprises a first bone contact surface extending along at least a portion of a top surface of the first endplate, and the second endplate comprises a second bone contact surface extending along at least a portion of a top surface of the second end plate.

7. The implant of claim 1, wherein the first end plate includes a first opening and the second endplate includes a second opening, such that the first and second openings collectively form a fusion aperture extending through the housing between the first and second endplates.

8. The implant of claim 7, wherein the wedge defines a wall of the fusion aperture such that the size of the fusion aperture increases as the implant is moved from the collapsed configuration to the expanded configuration.

9. The implant of claim 1, wherein the first and second ramps each has a radiused surface.

10. The implant of claim 9, wherein the first and second surfaces of the wedge each has a planar surface.

11. The implant of claim 1, wherein the drive mechanism includes a shaft with a first end rotatably coupled to the proximal wall of the housing and a second end threadedly coupled to the wedge.

12. The implant of claim 11, wherein the wedge comprises an aperture extending from a proximal face to a distal face of the wedge and dimensioned to receive the second end of the shaft of the drive mechanism.

13. An expandable implant, comprising:
   a housing having a proximal endwall, a distal endwall, an anterolateral sidewall, and a posterolateral sidewall defining a hollow interior;
   an upper endplate moveably attached to the housing and having a first interior surface including a first ramp, and a lower endplate moveably coupled to the housing and having a second interior surface including a second ramp;
   a wedge positioned at least partially within the hollow interior of the housing; and
   a drive mechanism configured to drive the wedge distally such that a first surface of the wedge engages the first ramp and a second surface of the wedge engages the second ramp, thereby moving the expandable implant from a collapsed configuration to an expanded configuration,
   wherein in the expanded configuration, a height between the upper and lower endplates increases from the proximal endwall toward the distal endwall and increases from the posterolateral sidewall toward the anterolateral sidewall, and
   wherein the upper and lower endplates each include: an interior side wall having a recess, and a projection configured to engage the wedge and lock the upper and lower endplates in the collapsed configuration.

14. The implant of claim 13, wherein the anterolateral sidewall has a length that is greater than a length of the posterolateral sidewall.

15. The implant of claim 13, wherein the drive mechanism includes a shaft with a first end rotatably coupled to the proximal endwall and a second end threadedly coupled to the wedge.

16. A method for adjusting an expandable implant in a subject, the method comprising:
   positioning the expandable implant in the subject, the expandable implant comprising:
      first and second endplates,
      a housing including a proximal wall and a distal wall opposite the proximal wall,
      an expansion mechanism, and
      a drive mechanism configured to engage the proximal wall of the housing,
      wherein the distal wall of the housing is free of the drive mechanism;
   engaging the drive mechanism with the expansion mechanism and driving the expansion mechanism relative to the housing,
      wherein the first and second endplates each include: an interior side wall having a recess, and a projection configured to engage the wedge and lock the first and second endplates in the collapsed configuration; and
   moving the expandable implant from a collapsed configuration to an expanded configuration and increasing a height between the first and second endplates in the expanded configuration, wherein the height increases along a direction from the proximal wall toward the distal wall of the housing.

17. The method of claim 16, wherein increasing the height between the first and second endplates in the expanded configuration further comprises increasing the height along a direction from the posterolateral sidewall toward the anterolateral sidewall of the housing.

18. The method of claim 16, wherein the drive mechanism includes a shaft having a first end and a second end opposite the first end, and the method further comprising rotatably coupling the first end of the shaft to the proximal wall of the housing and threadedly coupling the second end of the shaft to the expansion mechanism.

19. The method of claim 16, wherein the positioning further comprises inserting the implant into a disc space between adjacent vertebral bodies of the subject in the collapsed configuration.

* * * * *